(12) United States Patent
Taniguchi et al.

(10) Patent No.: US 6,365,361 B1
(45) Date of Patent: Apr. 2, 2002

(54) METHOD FOR IDENTIFYING OR SCREENING AGONIST AND ANTAGONIST TO PPAR

(75) Inventors: Tomoyasu Taniguchi, Toda; Junko Mizukami, Ootsu, both of (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/514,247

(22) Filed: Feb. 28, 2000

Related U.S. Application Data

(63) Continuation-in-part of application No. PCT/JP98/03734, filed on Aug. 24, 1998.

(30) Foreign Application Priority Data

Aug. 27, 1997 (JP) ............................................. 9-231084

(51) Int. Cl.[7] ...................... G01N 33/53; G01N 33/567; G01N 33/569; C12Q 1/02
(52) U.S. Cl. .......................... 435/7.2; 435/7.1; 435/7.21; 435/7.31; 435/29
(58) Field of Search ........................ 435/7.1, 7.2, 69.1, 435/69.9, 70.1, 71.1, 71.2, 471, 252.3, 29, 7.21, 7.31; 530/402

(56) References Cited

U.S. PATENT DOCUMENTS 5,283,173 A  2/1994  Fields et al.

OTHER PUBLICATIONS

Mizukami J, et al. The antidiabetic agent thiazolidinedione stimulates the interaction between PPARy and CBP. Biochem. Biophys. Res. Comm. 240:61–64, 1997.*

Zhu Y, et al. Cloning and identification of mouse steroid receptor coactivator-1 (mSRC-1), as a coactivator of peroxisome proliferator–activated receptor gamma. Gene Expression 6:185–195, 1996.*

Elbrecht A, et al. Molecular cloning, expression and characterization of human peroxisome proliferator activated receptors gamma1 and gamma2. Biochem. Biophys. Res. Comm. 224:431–437, 1996.*

Krey, "Fatty Acids, Eicosanoids, and Hypolipidemic Agents Identified as Ligands of Peroxisome Proliferator–Activated Receptors by Coactivator–Dependent Receptor Ligand Assay", Molecular Endocrinology, 1997, 779–791, 11(6).

* cited by examiner

Primary Examiner—Gary L. Kunz
Assistant Examiner—Robert S. Landsman
(74) Attorney, Agent, or Firm—Browdy and Neimark P.L.L.C.

(57) ABSTRACT

A method for identifying or screening an agonist for or antagonist to a peroxisome proliferator activated receptor (PPAR) which comprises allowing a test cell and a substance to be tested to coexist, and detecting a change in a ligand-dependent interaction between the PPAR and a coactivator in the test cells due to the substance to be tested by measuring the expression of a reporter gene as an index.

6 Claims, 3 Drawing Sheets

SEQUENCE LISTING

<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 1
tcccccgggt gctgttatgg gtgaaactct gggag    35

<210> SEQ ID NO 2
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 2
ccgctcgaga aatgttggca gtggctcagg actct    35

<210> SEQ ID NO 3
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 3
cgggatccgt atggccgaga acttgctgga cggac    35

<210> SEQ ID NO 4
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 4
gaagatcttc tctgttgccc tgcaccaaca gaacc    35

<210> SEQ ID NO 5
<211> LENGTH: 1679
<212> TYPE: DNA
<213> ORGANISM: Homo sapiens
<220> FEATURE:
<221> NAME/KEY: CDS
<222> LOCATION: (159)..(1679)

<400> SEQUENCE: 5

```
gccagaacca ccgcacgatg ttgctgtcgg ccacacagtg cttcagcagc gtgttcgact    60
tccagtcgtt caagtctttt cttttcacgg attgatcttt tgctagatag agacaaaata   120
tcagtgtgaa ttacagcaaa cccctattcc atgctgtt atg ggt gaa act ctg gga   176
                                          Met Gly Glu Thr Leu Gly
                                            1               5 gat tct cct att gac cca gaa agc gat tcc ttc act gat aca ctg tct   224
Asp Ser Pro Ile Asp Pro Glu Ser Asp Ser Phe Thr Asp Thr Leu Ser
         10                  15                  20 gca aac ata tca caa gaa atg acc atg gtt gac aca gag atc gca ttc   272
Ala Asn Ile Ser Gln Glu Met Thr Met Val Asp Thr Glu Ile Ala Phe
     25                  30                  35 tgg ccc acc aac ttt ggg atc agc tcc gtg gat ctc tcc gta atg gaa   320
Trp Pro Thr Asn Phe Gly Ile Ser Ser Val Asp Leu Ser Val Met Glu
 40                  45                  50 gac cac tcc cac tcc ttt gat atc aag ccc ttc act act gtt gac ttc   368
Asp His Ser His Ser Phe Asp Ile Lys Pro Phe Thr Thr Val Asp Phe
55                  60                  65                  70 tcc agc att tct act cca cat tac gaa gac att cca ttc aca aga aca   416
Ser Ser Ile Ser Thr Pro His Tyr Glu Asp Ile Pro Phe Thr Arg Thr
                 75                  80                  85 gat cca gtg gtt gca gat tac aag tat gac ctg aaa ctt caa gag tac   464
```

```
              Asp Pro Val Val Ala Asp Tyr Lys Tyr Asp Leu Lys Leu Gln Glu Tyr
                      90                  95                 100 caa agt gca atc aaa gtg gag cct gca tct cca cct tat tat tct gag         512
Gln Ser Ala Ile Lys Val Glu Pro Ala Ser Pro Pro Tyr Tyr Ser Glu
            105                 110                 115 aag act cag ctc tac aat aag cct cat gaa gag cct tcc aac tcc ctc         560
Lys Thr Gln Leu Tyr Asn Lys Pro His Glu Glu Pro Ser Asn Ser Leu
    120                 125                 130 atg gca att gaa tgt cgt gtc tgt gga gat aaa gct tct gga ttt cac         608
Met Ala Ile Glu Cys Arg Val Cys Gly Asp Lys Ala Ser Gly Phe His
135                 140                 145                 150 tat gga gtt cat gct tgt gaa gga tgc aag ggt ttc ttc cgg aga aca         656
Tyr Gly Val His Ala Cys Glu Gly Cys Lys Gly Phe Phe Arg Arg Thr
                155                 160                 165 atc aga ttg aag ctt atc tat gac aga tgt gat ctt aac tgt cgg atc         704
Ile Arg Leu Lys Leu Ile Tyr Asp Arg Cys Asp Leu Asn Cys Arg Ile
            170                 175                 180 cac aaa aaa agt aga aat aaa tgt cag tac tgt cgg ttt cag aaa tgc         752
His Lys Lys Ser Arg Asn Lys Cys Gln Tyr Cys Arg Phe Gln Lys Cys
    185                 190                 195 ctt gca gtg ggg atg tct cat aat gcc atc agg ttt ggg cgg atc gca         800
Leu Ala Val Gly Met Ser His Asn Ala Ile Arg Phe Gly Arg Ile Ala
200                 205                 210 cag gcc gag aag gag aag ctg ttg gcg gag atc tcc agt gat atc gac         848
Gln Ala Glu Lys Glu Lys Leu Leu Ala Glu Ile Ser Ser Asp Ile Asp
215                 220                 225                 230 cag ctc aat cca gag tcc gct gac ctc cgt cag gcc ctg gca aaa cat         896
Gln Leu Asn Pro Glu Ser Ala Asp Leu Arg Gln Ala Leu Ala Lys His
                235                 240                 245 ttg tat gac tca tac ata aag tcc ttc ccg ctg acc aaa gca aag gcg         944
Leu Tyr Asp Ser Tyr Ile Lys Ser Phe Pro Leu Thr Lys Ala Lys Ala
            250                 255                 260 agg gcg atc ttg aca gga aag aca aca gac aaa tca cca ttc gtt atc         992
Arg Ala Ile Leu Thr Gly Lys Thr Thr Asp Lys Ser Pro Phe Val Ile
    265                 270                 275 tat gac atg aat tcc tta atg atg gga gaa gat aaa atc aag ttc aaa        1040
Tyr Asp Met Asn Ser Leu Met Met Gly Glu Asp Lys Ile Lys Phe Lys
280                 285                 290 cac atc acc ccc ctg cag gag cag agc aaa gag gtg gcc atc cgc atc        1088
His Ile Thr Pro Leu Gln Glu Gln Ser Lys Glu Val Ala Ile Arg Ile
295                 300                 305                 310 ttt cag ggc tgc cag ttt cgc tcc gtg gag gct gtg cag gag atc aca        1136
Phe Gln Gly Cys Gln Phe Arg Ser Val Glu Ala Val Gln Glu Ile Thr
                315                 320                 325 gag tat gcc aaa agc att cct ggt ttt gta aat ctt gac ttg aac gac        1184
Glu Tyr Ala Lys Ser Ile Pro Gly Phe Val Asn Leu Asp Leu Asn Asp
            330                 335                 340 caa gta act ctc ctc aaa tat gga gtc cac gag atc att tac aca atg        1232
Gln Val Thr Leu Leu Lys Tyr Gly Val His Glu Ile Ile Tyr Thr Met
    345                 350                 355 ctg gcc tcc ttg atg aat aaa gat ggg gtt ctc ata tcc gag ggc caa        1280
Leu Ala Ser Leu Met Asn Lys Asp Gly Val Leu Ile Ser Glu Gly Gln
360                 365                 370 ggc ttc atg aca agg gag ttt cta aag agc ctg cga aag cct ttt ggt        1328
Gly Phe Met Thr Arg Glu Phe Leu Lys Ser Leu Arg Lys Pro Phe Gly
375                 380                 385                 390 gac ttt atg gag ccc aag ttt gag ttt gct gtg aag ttc aat gca ctg        1376
Asp Phe Met Glu Pro Lys Phe Glu Phe Ala Val Lys Phe Asn Ala Leu
                395                 400                 405
```

```
gaa tta gat gac agc gac ttg gca ata ttt att gct gtc att att ctc     1424
Glu Leu Asp Asp Ser Asp Leu Ala Ile Phe Ile Ala Val Ile Ile Leu
            410                 415                 420 agt gga gac cgc cca ggt ttg ctg aat gtg aag ccc att gaa gac att     1472
Ser Gly Asp Arg Pro Gly Leu Leu Asn Val Lys Pro Ile Glu Asp Ile
        425                 430                 435 caa gac aac ctg cta caa gcc ctg gag ctc cag ctg aag ctg aac cat     1520
Gln Asp Asn Leu Leu Gln Ala Leu Glu Leu Gln Leu Lys Leu Asn His
440                 445                 450 cct gag tcc tca cag ctg ttt gcc aag ctg ctc cag aaa atg aca gac     1568
Pro Glu Ser Ser Gln Leu Phe Ala Lys Leu Leu Gln Lys Met Thr Asp
455                 460                 465                 470 ctc aga cag att gtc acg gaa cac gtg cag cta ctg cag gtg atc aag     1616
Leu Arg Gln Ile Val Thr Glu His Val Gln Leu Leu Gln Val Ile Lys
                475                 480                 485 aag acg gag aca gac atg agt ctt cac ccg ctc ctg cag gag atc tac     1664
Lys Thr Glu Thr Asp Met Ser Leu His Pro Leu Leu Gln Glu Ile Tyr
            490                 495                 500 aag gac ttg tac tag                                                 1679
Lys Asp Leu Tyr
        505
```

<210> SEQ ID NO 6
<211> LENGTH: 506
<212> TYPE: PRT
<213> ORGANISM: Homo sapiens

<400> SEQUENCE: 6

```
Met Gly Glu Thr Leu Gly Asp Ser Pro Ile Asp Pro Glu Ser Asp Ser
1               5                   10                  15

Phe Thr Asp Thr Leu Ser Ala Asn Ile Ser Gln Glu Met Thr Met Val
                20                  25                  30

Asp Thr Glu Ile Ala Phe Trp Pro Thr Asn Phe Gly Ile Ser Ser Val
            35                  40                  45

Asp Leu Ser Val Met Glu Asp His Ser His Ser Phe Asp Ile Lys Pro
        50                  55                  60

Phe Thr Thr Val Asp Phe Ser Ser Ile Ser Thr Pro His Tyr Glu Asp
65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Lys Pro His Glu
        115                 120                 125

Glu Pro Ser Asn Ser Leu Met Ala Ile Glu Cys Arg Val Cys Gly Asp
    130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Ile Ala Gln Ala Glu Lys Glu Lys Leu Leu Ala Glu
    210                 215                 220

Ile Ser Ser Asp Ile Asp Gln Leu Asn Pro Glu Ser Ala Asp Leu Arg
```

-continued

```
                225                 230                 235                 240
Gln Ala Leu Ala Lys His Leu Tyr Asp Ser Tyr Ile Lys Ser Phe Pro
                    245                 250                 255
Leu Thr Lys Ala Lys Ala Arg Ala Ile Leu Thr Gly Lys Thr Thr Asp
                260                 265                 270
Lys Ser Pro Phe Val Ile Tyr Asp Met Asn Ser Leu Met Met Gly Glu
            275                 280                 285
Asp Lys Ile Lys Phe Lys His Ile Thr Pro Leu Gln Glu Gln Ser Lys
        290                 295                 300
Glu Val Ala Ile Arg Ile Phe Gln Gly Cys Gln Phe Arg Ser Val Glu
305                 310                 315                 320
Ala Val Gln Glu Ile Thr Glu Tyr Ala Lys Ser Ile Pro Gly Phe Val
                325                 330                 335
Asn Leu Asp Leu Asn Asp Gln Val Thr Leu Leu Lys Tyr Gly Val His
                340                 345                 350
Glu Ile Ile Tyr Thr Met Leu Ala Ser Leu Met Asn Lys Asp Gly Val
                355                 360                 365
Leu Ile Ser Glu Gly Gln Gly Phe Met Thr Arg Glu Phe Leu Lys Ser
    370                 375                 380
Leu Arg Lys Pro Phe Gly Asp Phe Met Glu Pro Lys Phe Glu Phe Ala
385                 390                 395                 400
Val Lys Phe Asn Ala Leu Glu Leu Asp Asp Ser Asp Leu Ala Ile Phe
                405                 410                 415
Ile Ala Val Ile Ile Leu Ser Gly Asp Arg Pro Gly Leu Leu Asn Val
                420                 425                 430
Lys Pro Ile Glu Asp Ile Gln Asp Asn Leu Leu Gln Ala Leu Glu Leu
            435                 440                 445
Gln Leu Lys Leu Asn His Pro Glu Ser Ser Gln Leu Phe Ala Lys Leu
        450                 455                 460
Leu Gln Lys Met Thr Asp Leu Arg Gln Ile Val Thr Glu His Val Gln
465                 470                 475                 480
Leu Leu Gln Val Ile Lys Lys Thr Glu Thr Asp Met Ser Leu His Pro
                485                 490                 495
Leu Leu Gln Glu Ile Tyr Lys Asp Leu Tyr
                500                 505
```

<210> SEQ ID NO 7
<211> LENGTH: 7326
<212> TYPE: DNA
<213> ORGANISM: mouse
<220> FEATURE:
<221> NAME/KEY: CDS
<222> LOCATION: (1)..(7326)
<223> OTHER INFORMATION: n at position 1131 is unknown.

<400> SEQUENCE: 7

```
atg gcc gag aac ttg ctg gac gga ccg ccc aac ccc aaa cga gcc aaa      48
Met Ala Glu Asn Leu Leu Asp Gly Pro Pro Asn Pro Lys Arg Ala Lys
1               5                   10                  15 ctc agc tcg ccc ggc ttc tcc gcg aat gac aac aca gat ttt gga tca      96
Leu Ser Ser Pro Gly Phe Ser Ala Asn Asp Asn Thr Asp Phe Gly Ser
                20                  25                  30 ttg ttt gac ttg gaa aat gac ctt cct gat gag ctg atc ccc aat gga     144
Leu Phe Asp Leu Glu Asn Asp Leu Pro Asp Glu Leu Ile Pro Asn Gly
            35                  40                  45 gaa tta agc ctt tta aac agt ggg aac ctt gtt cca gat gct gcg tcc     192
Glu Leu Ser Leu Leu Asn Ser Gly Asn Leu Val Pro Asp Ala Ala Ser
```

```
              50                  55                  60
aaa cat aaa caa ctg tca gag ctt ctt aga gga ggc agc ggc tct agc         240
Lys His Lys Gln Leu Ser Glu Leu Leu Arg Gly Gly Ser Gly Ser Ser
 65                  70                  75                  80 atc aac cca ggg ata ggc aat gtg agt gcc agc agc cct gtg caa cag         288
Ile Asn Pro Gly Ile Gly Asn Val Ser Ala Ser Ser Pro Val Gln Gln
                 85                  90                  95 ggc ctt ggt ggc cag gct cag ggg cag ccg aac agt aca aac atg gcc         336
Gly Leu Gly Gly Gln Ala Gln Gly Gln Pro Asn Ser Thr Asn Met Ala
                100                 105                 110 agc tta ggt gcc atg ggc aag agc cct ctg aac caa gga gac tca tca         384
Ser Leu Gly Ala Met Gly Lys Ser Pro Leu Asn Gln Gly Asp Ser Ser
            115                 120                 125 aca ccc aac ctg ccc aaa cag gca gcc agc acc tct ggg ccc act ccc         432
Thr Pro Asn Leu Pro Lys Gln Ala Ala Ser Thr Ser Gly Pro Thr Pro
        130                 135                 140 cct gcc tcc caa gca ctg aat cca caa gca caa aag caa gta ggg ctg         480
Pro Ala Ser Gln Ala Leu Asn Pro Gln Ala Gln Lys Gln Val Gly Leu
145                 150                 155                 160 gtg acc agt agt cct gcc aca tca cag act gga cct ggg atc tgc atg         528
Val Thr Ser Ser Pro Ala Thr Ser Gln Thr Gly Pro Gly Ile Cys Met
                165                 170                 175 aat gct aac ttc aac cag acc cac cca ggc ctt ctc aat agt aac tct         576
Asn Ala Asn Phe Asn Gln Thr His Pro Gly Leu Leu Asn Ser Asn Ser
            180                 185                 190 ggc cat agc tta atg aat cag gct caa caa ggg caa gct caa gtc atg         624
Gly His Ser Leu Met Asn Gln Ala Gln Gln Gly Gln Ala Gln Val Met
        195                 200                 205 aat gga tct ctt ggg gct gct gga aga gga agg gga gct gga atg ccc         672
Asn Gly Ser Leu Gly Ala Ala Gly Arg Gly Arg Gly Ala Gly Met Pro
    210                 215                 220 tac cct gct cca gcc atg cag ggg gcc aca agc agt gtg ctg gcg gag         720
Tyr Pro Ala Pro Ala Met Gln Gly Ala Thr Ser Ser Val Leu Ala Glu
225                 230                 235                 240 acc ttg aca cag gtt tcc cca caa atg gct ggc cat gct gga cta aat         768
Thr Leu Thr Gln Val Ser Pro Gln Met Ala Gly His Ala Gly Leu Asn
                245                 250                 255 aca gca cag gca gga ggc atg acc aag atg gga atg act ggt acc aca         816
Thr Ala Gln Ala Gly Gly Met Thr Lys Met Gly Met Thr Gly Thr Thr
            260                 265                 270 agt cca ttt gga caa ccc ttt agt caa act gga ggg cag cag atg gga         864
Ser Pro Phe Gly Gln Pro Phe Ser Gln Thr Gly Gly Gln Gln Met Gly
        275                 280                 285 gcc act gga gtg aac ccc cag tta gcc agc aaa cag agc atg gtc aat         912
Ala Thr Gly Val Asn Pro Gln Leu Ala Ser Lys Gln Ser Met Val Asn
    290                 295                 300 agt tta cct gct ttt cct aca gat atc aag aat act tca gtc acc act         960
Ser Leu Pro Ala Phe Pro Thr Asp Ile Lys Asn Thr Ser Val Thr Thr
305                 310                 315                 320 gtg cca aat atg tcc cag ttg caa aca tca gtg gga att gta ccc aca        1008
Val Pro Asn Met Ser Gln Leu Gln Thr Ser Val Gly Ile Val Pro Thr
                325                 330                 335 caa gca att gca aca ggc ccc aca gca gac cct gaa aaa cgc aaa ctg        1056
Gln Ala Ile Ala Thr Gly Pro Thr Ala Asp Pro Glu Lys Arg Lys Leu
            340                 345                 350 ata cag cag cag ctg gtt cta ctg ctt cat gcc cac aaa tgt cag aga        1104
Ile Gln Gln Gln Leu Val Leu Leu Leu His Ala His Lys Cys Gln Arg
        355                 360                 365 cga gag caa gca aat gga gag gtt cgn gcc tgt tct ctc cca cac tgt        1152
```

```
                                                           -continued

Arg Glu Gln Ala Asn Gly Glu Val Arg Ala Cys Ser Leu Pro His Cys
    370                 375                 380 cga acc atg aaa aac gtt ttg aat cac atg aca cat tgt cag gct ccc          1200
Arg Thr Met Lys Asn Val Leu Asn His Met Thr His Cys Gln Ala Pro
385                 390                 395                 400 aaa gcc tgc caa gtt gcc cat tgt gca tct tca cga caa atc atc tct          1248
Lys Ala Cys Gln Val Ala His Cys Ala Ser Ser Arg Gln Ile Ile Ser
                405                 410                 415 cat tgg aag aac tgc aca cga cat gac tgt cct gtt tgc ctc cct ttg          1296
His Trp Lys Asn Cys Thr Arg His Asp Cys Pro Val Cys Leu Pro Leu
            420                 425                 430 aaa aat gcc agt gac aag cga aac caa caa acc atc ctg gga tct cca          1344
Lys Asn Ala Ser Asp Lys Arg Asn Gln Gln Thr Ile Leu Gly Ser Pro
        435                 440                 445 gct agt gga att caa aac aca att ggt tct gtt ggt gca ggg caa cag          1392
Ala Ser Gly Ile Gln Asn Thr Ile Gly Ser Val Gly Ala Gly Gln Gln
    450                 455                 460 aat gcc act tcc tta agt aac cca aat ccc ata gac ccc agt tcc atg          1440
Asn Ala Thr Ser Leu Ser Asn Pro Asn Pro Ile Asp Pro Ser Ser Met
465                 470                 475                 480 cag cgg gcc tat gct gct cta gga ctc ccc tac atg aac cag cct cag          1488
Gln Arg Ala Tyr Ala Ala Leu Gly Leu Pro Tyr Met Asn Gln Pro Gln
                485                 490                 495 acg cag ctg cag cct cag gtt cct ggc cag caa cca gca cag cct cca          1536
Thr Gln Leu Gln Pro Gln Val Pro Gly Gln Gln Pro Ala Gln Pro Pro
            500                 505                 510 gcc cac cag cag atg agg act ctc aat gcc cta gga aac aac ccc atg          1584
Ala His Gln Gln Met Arg Thr Leu Asn Ala Leu Gly Asn Asn Pro Met
        515                 520                 525 agt gtc cca gca gga gga ata aca aca gat caa cag cca cca aac ttg          1632
Ser Val Pro Ala Gly Gly Ile Thr Thr Asp Gln Gln Pro Pro Asn Leu
    530                 535                 540 att tca gaa tca gct ctt cca act tcc ttg ggg gct acc aat cca ctg          1680
Ile Ser Glu Ser Ala Leu Pro Thr Ser Leu Gly Ala Thr Asn Pro Leu
545                 550                 555                 560 atg aat gat ggt tca aac tct ggt aac att gga agc ctc agc acg ata          1728
Met Asn Asp Gly Ser Asn Ser Gly Asn Ile Gly Ser Leu Ser Thr Ile
                565                 570                 575 cct aca gca gcg cct cct tcc agc act ggt gtt cga aaa ggc tgg cat          1776
Pro Thr Ala Ala Pro Pro Ser Ser Thr Gly Val Arg Lys Gly Trp His
            580                 585                 590 gaa cat gtg act cag gac cta cgg agt cat cta gtc cat aaa ctc gtt          1824
Glu His Val Thr Gln Asp Leu Arg Ser His Leu Val His Lys Leu Val
        595                 600                 605 caa gcc atc ttc cca act cca gac cct gca gct ctg aaa gat cgc cgc          1872
Gln Ala Ile Phe Pro Thr Pro Asp Pro Ala Ala Leu Lys Asp Arg Arg
    610                 615                 620 atg gag aac ctg gtt gcc tat gct aag aaa gtg gag gga gac atg tat          1920
Met Glu Asn Leu Val Ala Tyr Ala Lys Lys Val Glu Gly Asp Met Tyr
625                 630                 635                 640 gag tct gct aat agc agg gat gaa tac tat cat tta tta gca gag aaa          1968
Glu Ser Ala Asn Ser Arg Asp Glu Tyr Tyr His Leu Leu Ala Glu Lys
                645                 650                 655 atc tat aaa ata caa aaa gaa cta gaa gaa aag cgg agg aca cgt tta          2016
Ile Tyr Lys Ile Gln Lys Glu Leu Glu Glu Lys Arg Arg Thr Arg Leu
            660                 665                 670 cat aag caa ggc atc ctg ggt aac cag cca gct tta cca gct tct ggg          2064
His Lys Gln Gly Ile Leu Gly Asn Gln Pro Ala Leu Pro Ala Ser Gly
        675                 680                 685
```

-continued

```
gct cag ccc cct gtg att cca cca gcc cag tct gta aga cct cca aat      2112
Ala Gln Pro Pro Val Ile Pro Pro Ala Gln Ser Val Arg Pro Pro Asn
    690             695                 700 ggg ccc ctg cct ttg cca gtg aat cgc atg cag gtt tct caa ggg atg      2160
Gly Pro Leu Pro Leu Pro Val Asn Arg Met Gln Val Ser Gln Gly Met
705                 710                 715                 720 aat tca ttt aac cca atg tcc ctg gga aac gtc cag ttg cca cag gca      2208
Asn Ser Phe Asn Pro Met Ser Leu Gly Asn Val Gln Leu Pro Gln Ala
                725                 730                 735 ccc atg gga cct cgt gca gcc tcc cct atg aac cac tct gtg cag atg      2256
Pro Met Gly Pro Arg Ala Ala Ser Pro Met Asn His Ser Val Gln Met
            740                 745                 750 aac agc atg gcc tca gtt ccg ggt atg gcc att tct cct tca cgg atg      2304
Asn Ser Met Ala Ser Val Pro Gly Met Ala Ile Ser Pro Ser Arg Met
        755                 760                 765 cct cag cct cca aat atg atg ggc act cat gcc aac aac att atg gcc      2352
Pro Gln Pro Pro Asn Met Met Gly Thr His Ala Asn Asn Ile Met Ala
    770                 775                 780 cag gca cct act cag aac cag ttt ctg cca cag aac cag ttt cca tca      2400
Gln Ala Pro Thr Gln Asn Gln Phe Leu Pro Gln Asn Gln Phe Pro Ser
785                 790                 795                 800 tcc agt ggg gca atg agt gtg aac agt gtg ggc atg ggg caa cca gca      2448
Ser Ser Gly Ala Met Ser Val Asn Ser Val Gly Met Gly Gln Pro Ala
                805                 810                 815 gcc cag gca ggt gtt tca cag ggt cag gaa cct gga gct gct ctc cct      2496
Ala Gln Ala Gly Val Ser Gln Gly Gln Glu Pro Gly Ala Ala Leu Pro
            820                 825                 830 aac cct ctg aac atg ctg gca ccc cag gcc agc cag ctg cct tgc cca      2544
Asn Pro Leu Asn Met Leu Ala Pro Gln Ala Ser Gln Leu Pro Cys Pro
        835                 840                 845 cca gtg aca cag tca cca ttg cac ccg act cca cct cct gct tcc aca      2592
Pro Val Thr Gln Ser Pro Leu His Pro Thr Pro Pro Pro Ala Ser Thr
    850                 855                 860 gct gct ggc atg ccc tct ctc caa cat cca acg gca cca gga atg acc      2640
Ala Ala Gly Met Pro Ser Leu Gln His Pro Thr Ala Pro Gly Met Thr
865                 870                 875                 880 cct cct cag cca gca gct ccc act cag cca tct act cct gtg tca tct      2688
Pro Pro Gln Pro Ala Ala Pro Thr Gln Pro Ser Thr Pro Val Ser Ser
                885                 890                 895 ggg cag act cct acc cca act cct ggc tca gtg ccc agc gct gcc caa      2736
Gly Gln Thr Pro Thr Pro Thr Pro Gly Ser Val Pro Ser Ala Ala Gln
            900                 905                 910 aca cag agt acc cct aca gtc cag gca gca gca cag gct cag gtg act      2784
Thr Gln Ser Thr Pro Thr Val Gln Ala Ala Ala Gln Ala Gln Val Thr
        915                 920                 925 cca cag cct cag acc cca gtg cag cca cca tct gtg gct act cct cag      2832
Pro Gln Pro Gln Thr Pro Val Gln Pro Pro Ser Val Ala Thr Pro Gln
    930                 935                 940 tca tca cag cag caa cca acg cct gtg cat act cag cca cct ggc aca      2880
Ser Ser Gln Gln Gln Pro Thr Pro Val His Thr Gln Pro Pro Gly Thr
945                 950                 955                 960 ccg ctt tct cag gca gca gcc agc att gat aat aga gtc cct act ccc      2928
Pro Leu Ser Gln Ala Ala Ala Ser Ile Asp Asn Arg Val Pro Thr Pro
                965                 970                 975 tcc act gtg acc agt gct gaa acc agt tcc cag cag cca gga ccc gat      2976
Ser Thr Val Thr Ser Ala Glu Thr Ser Ser Gln Gln Pro Gly Pro Asp
            980                 985                 990 gtg ccc atg ctg gaa atg aag aca  gag gtg cag aca  gat gat gct gag    3024
Val Pro Met Leu Glu Met Lys Thr  Glu Val Gln Thr  Asp Asp Ala Glu
        995                 1000                 1005
```

-continued

| | | | | | | | | | | |
|---|---|---|---|---|---|---|---|---|---|---|
| cct | gaa | cct | act | gaa | tcc | aag | ggg | gaa | cct | cgg | tct | gag | atg | atg | 3069 |
| Pro | Glu | Pro | Thr | Glu | Ser | Lys | Gly | Glu | Pro | Arg | Ser | Glu | Met | Met | |
| | 1010 | | | | 1015 | | | | | 1020 | | | | | |

| gaa | gag | gat | tta | caa | ggt | tct | tcc | caa | gta | aaa | gaa | gag | aca | gat | 3114 |
| Glu | Glu | Asp | Leu | Gln | Gly | Ser | Ser | Gln | Val | Lys | Glu | Glu | Thr | Asp | |
| 1025 | | | | | 1030 | | | | | 1035 | | | | | |

| acg | aca | gag | cag | aag | tca | gag | cca | atg | gaa | gta | gaa | gaa | aag | aaa | 3159 |
| Thr | Thr | Glu | Gln | Lys | Ser | Glu | Pro | Met | Glu | Val | Glu | Glu | Lys | Lys | |
| 1040 | | | | | 1045 | | | | | 1050 | | | | | |

| cct | gaa | gta | aaa | gtg | gaa | gct | aaa | gag | gaa | gaa | gag | aac | agt | tcg | 3204 |
| Pro | Glu | Val | Lys | Val | Glu | Ala | Lys | Glu | Glu | Glu | Glu | Asn | Ser | Ser | |
| 1055 | | | | | 1060 | | | | | 1065 | | | | | |

| aac | gac | aca | gcc | tca | caa | tca | aca | tct | cct | tcc | cag | cca | cgc | aaa | 3249 |
| Asn | Asp | Thr | Ala | Ser | Gln | Ser | Thr | Ser | Pro | Ser | Gln | Pro | Arg | Lys | |
| 1070 | | | | | 1075 | | | | | 1080 | | | | | |

| aaa | atc | ttt | aaa | ccc | gag | gag | cta | cgc | cag | gca | ctt | atg | cca | act | 3294 |
| Lys | Ile | Phe | Lys | Pro | Glu | Glu | Leu | Arg | Gln | Ala | Leu | Met | Pro | Thr | |
| 1085 | | | | | 1090 | | | | | 1095 | | | | | |

| cta | gaa | gca | ctc | tat | cga | cag | gac | cca | gag | tct | ttg | cct | ttt | cgt | 3339 |
| Leu | Glu | Ala | Leu | Tyr | Arg | Gln | Asp | Pro | Glu | Ser | Leu | Pro | Phe | Arg | |
| 1100 | | | | | 1105 | | | | | 1110 | | | | | |

| cag | cct | gta | gat | cct | cag | ctc | cta | gga | atc | cca | gat | tat | ttt | gat | 3384 |
| Gln | Pro | Val | Asp | Pro | Gln | Leu | Leu | Gly | Ile | Pro | Asp | Tyr | Phe | Asp | |
| 1115 | | | | | 1120 | | | | | 1125 | | | | | |

| ata | gtg | aag | aat | cct | atg | gac | ctt | tct | acc | atc | aaa | cga | aag | ctg | 3429 |
| Ile | Val | Lys | Asn | Pro | Met | Asp | Leu | Ser | Thr | Ile | Lys | Arg | Lys | Leu | |
| 1130 | | | | | 1135 | | | | | 1140 | | | | | |

| gac | aca | ggg | caa | tat | caa | gaa | ccc | tgg | cag | tat | gtg | gat | gat | gtc | 3474 |
| Asp | Thr | Gly | Gln | Tyr | Gln | Glu | Pro | Trp | Gln | Tyr | Val | Asp | Asp | Val | |
| 1145 | | | | | 1150 | | | | | 1155 | | | | | |

| agg | ctt | atg | ttc | aac | aat | gcg | tgg | cta | tat | aat | cgt | aaa | acg | tcc | 3519 |
| Arg | Leu | Met | Phe | Asn | Asn | Ala | Trp | Leu | Tyr | Asn | Arg | Lys | Thr | Ser | |
| 1160 | | | | | 1165 | | | | | 1170 | | | | | |

| cgt | gta | tat | aaa | ttt | tgc | agt | aaa | ctt | gca | gag | gtc | ttt | gaa | caa | 3564 |
| Arg | Val | Tyr | Lys | Phe | Cys | Ser | Lys | Leu | Ala | Glu | Val | Phe | Glu | Gln | |
| 1175 | | | | | 1180 | | | | | 1185 | | | | | |

| gaa | att | gac | cct | gtc | atg | cag | tct | ctt | gga | tat | tgc | tgt | gga | cga | 3609 |
| Glu | Ile | Asp | Pro | Val | Met | Gln | Ser | Leu | Gly | Tyr | Cys | Cys | Gly | Arg | |
| 1190 | | | | | 1195 | | | | | 1200 | | | | | |

| aag | tat | gag | ttc | tcc | cca | cag | act | ttg | tgc | tgt | tac | gga | aag | cag | 3654 |
| Lys | Tyr | Glu | Phe | Ser | Pro | Gln | Thr | Leu | Cys | Cys | Tyr | Gly | Lys | Gln | |
| 1205 | | | | | 1210 | | | | | 1215 | | | | | |

| ctg | tgt | aca | att | cct | cgt | gat | gca | gcc | tac | tac | agc | tat | cag | aat | 3699 |
| Leu | Cys | Thr | Ile | Pro | Arg | Asp | Ala | Ala | Tyr | Tyr | Ser | Tyr | Gln | Asn | |
| 1220 | | | | | 1225 | | | | | 1230 | | | | | |

| agg | tat | cat | ttc | tgt | ggg | aag | tgt | ttc | aca | gag | atc | cag | ggc | gag | 3744 |
| Arg | Tyr | His | Phe | Cys | Gly | Lys | Cys | Phe | Thr | Glu | Ile | Gln | Gly | Glu | |
| 1235 | | | | | 1240 | | | | | 1245 | | | | | |

| aat | gtg | acc | ctg | ggt | gac | gac | cct | tcc | caa | cct | cag | acg | aca | att | 3789 |
| Asn | Val | Thr | Leu | Gly | Asp | Asp | Pro | Ser | Gln | Pro | Gln | Thr | Thr | Ile | |
| 1250 | | | | | 1255 | | | | | 1260 | | | | | |

| tcc | aag | gat | caa | ttt | gaa | aag | aag | aaa | aat | gat | acc | tta | gat | cct | 3834 |
| Ser | Lys | Asp | Gln | Phe | Glu | Lys | Lys | Lys | Asn | Asp | Thr | Leu | Asp | Pro | |
| 1265 | | | | | 1270 | | | | | 1275 | | | | | |

| gaa | cct | ttt | gtt | gac | tgc | aaa | gag | tgt | ggc | cgg | aag | atg | cat | cag | 3879 |
| Glu | Pro | Phe | Val | Asp | Cys | Lys | Glu | Cys | Gly | Arg | Lys | Met | His | Gln | |
| 1280 | | | | | 1285 | | | | | 1290 | | | | | |

| att | tgt | gtt | cta | cac | tat | gac | atc | att | tgg | cct | tca | ggt | ttt | gtg | 3924 |
| Ile | Cys | Val | Leu | His | Tyr | Asp | Ile | Ile | Trp | Pro | Ser | Gly | Phe | Val | |

```
                1295                1300                1305
tgt gac aac tgt ttg aag aaa act ggc aga cct cgg aaa gaa aac      3969
Cys Asp Asn Cys Leu Lys Lys Thr Gly Arg Pro Arg Lys Glu Asn
    1310                1315                1320 aaa ttc agt gct aag agg ctg cag acc aca cga ttg gga aac cac      4014
Lys Phe Ser Ala Lys Arg Leu Gln Thr Thr Arg Leu Gly Asn His
    1325                1330                1335 tta gaa gac aga gtg aat aag ttt ttg cgg cgc cag aat cac cct      4059
Leu Glu Asp Arg Val Asn Lys Phe Leu Arg Arg Gln Asn His Pro
    1340                1345                1350 gaa gct ggg gag gtt ttt gtc aga gtg gtg gcc agc tca gac aag      4104
Glu Ala Gly Glu Val Phe Val Arg Val Val Ala Ser Ser Asp Lys
    1355                1360                1365 act gtg gag gtc aag ccg gga atg aag tca agg ttt gtg gat tct      4149
Thr Val Glu Val Lys Pro Gly Met Lys Ser Arg Phe Val Asp Ser
    1370                1375                1380 gga gag atg tcg gaa tct ttc cca tat cgt acc aaa gca ctc ttt      4194
Gly Glu Met Ser Glu Ser Phe Pro Tyr Arg Thr Lys Ala Leu Phe
    1385                1390                1395 gct ttt gag gag atc gat gga gtc gat gtg tgc ttt ttt ggg atg      4239
Ala Phe Glu Glu Ile Asp Gly Val Asp Val Cys Phe Phe Gly Met
    1400                1405                1410 cat gtg caa gat acg gct ctg att gcc ccc cac caa ata caa ggc      4284
His Val Gln Asp Thr Ala Leu Ile Ala Pro His Gln Ile Gln Gly
    1415                1420                1425 tgt gta tac ata tct tat ctg gac agt att cat ttc ttc cgg ccc      4329
Cys Val Tyr Ile Ser Tyr Leu Asp Ser Ile His Phe Phe Arg Pro
    1430                1435                1440 cgc tgc ctc cgg aca gct gtt tac cat gag atc ctc atc gga tat      4374
Arg Cys Leu Arg Thr Ala Val Tyr His Glu Ile Leu Ile Gly Tyr
    1445                1450                1455 ctc gag tat gtg aag aaa ttg gtg tat gtg aca gca cat att tgg      4419
Leu Glu Tyr Val Lys Lys Leu Val Tyr Val Thr Ala His Ile Trp
    1460                1465                1470 gcc tgt ccc cca agt gaa gga gat gac tat atc ttt cat tgc cac      4464
Ala Cys Pro Pro Ser Glu Gly Asp Asp Tyr Ile Phe His Cys His
    1475                1480                1485 ccc cct gac cag aaa atc ccc aaa cca aaa cga cta cag gag tgg      4509
Pro Pro Asp Gln Lys Ile Pro Lys Pro Lys Arg Leu Gln Glu Trp
    1490                1495                1500 tac aag aag atg ctg gac aag gcg ttt gca gag agg atc att aac      4554
Tyr Lys Lys Met Leu Asp Lys Ala Phe Ala Glu Arg Ile Ile Asn
    1505                1510                1515 gac tat aag gac atc ttc aaa caa gcg aac gaa gac agg ctc acg      4599
Asp Tyr Lys Asp Ile Phe Lys Gln Ala Asn Glu Asp Arg Leu Thr
    1520                1525                1530 agt gcc aag gag ttg ccc tat ttt gaa gga gat ttc tgg cct aat      4644
Ser Ala Lys Glu Leu Pro Tyr Phe Glu Gly Asp Phe Trp Pro Asn
    1535                1540                1545 gtg ttg gaa gaa agc att aag gaa cta gaa caa gaa gaa gaa gaa      4689
Val Leu Glu Glu Ser Ile Lys Glu Leu Glu Gln Glu Glu Glu Glu
    1550                1555                1560 agg aaa aaa gaa gag agt act gca gcg agt gag act cct gag ggc      4734
Arg Lys Lys Glu Glu Ser Thr Ala Ala Ser Glu Thr Pro Glu Gly
    1565                1570                1575 agt cag ggt gac agc aaa aat gcg aag aaa aag aac aac aag aag      4779
Ser Gln Gly Asp Ser Lys Asn Ala Lys Lys Lys Asn Asn Lys Lys
    1580                1585                1590 acc aac aaa aac aaa agc agc att agc cgc gcc aac aag aag aag      4824
```

```
                                    -continued

Thr Asn Lys Asn Lys Ser Ser Ile Ser Arg Ala Asn Lys Lys Lys
    1595            1600                1605 ccc agc atg ccc aat gtt tcc aac gac ctg tcg cag aag ctg tat         4869
Pro Ser Met Pro Asn Val Ser Asn Asp Leu Ser Gln Lys Leu Tyr
    1610            1615                1620 gcc acc atg gag aag cac aag gag gta ttc ttt gtg att cat ctg         4914
Ala Thr Met Glu Lys His Lys Glu Val Phe Phe Val Ile His Leu
    1625            1630                1635 cat gct ggg cct gtt atc agc act cag ccc ccc atc gtg gac cct         4959
His Ala Gly Pro Val Ile Ser Thr Gln Pro Pro Ile Val Asp Pro
    1640            1645                1650 gat cct ctg ctt agc tgt gac ctc atg gat ggg cga gat gcc ttc         5004
Asp Pro Leu Leu Ser Cys Asp Leu Met Asp Gly Arg Asp Ala Phe
    1655            1660                1665 ctc acc ctg gcc aga gac aag cac tgg gaa ttc tct tcc tta cgc         5049
Leu Thr Leu Ala Arg Asp Lys His Trp Glu Phe Ser Ser Leu Arg
    1670            1675                1680 cgc tcc aaa tgg tcc act ctg tgc atg ctg gtg gag ctg cac aca         5094
Arg Ser Lys Trp Ser Thr Leu Cys Met Leu Val Glu Leu His Thr
    1685            1690                1695 cag ggc cag gac cgc ttt gtt tat acc tgc aat gag tgc aaa cac         5139
Gln Gly Gln Asp Arg Phe Val Tyr Thr Cys Asn Glu Cys Lys His
    1700            1705                1710 cat gtg gaa aca cgc tgg cac tgc act gtg tgt gag gac tat gac         5184
His Val Glu Thr Arg Trp His Cys Thr Val Cys Glu Asp Tyr Asp
    1715            1720                1725 ctt tgt atc aat tgc tac aac aca aag agc cac acc cat aag atg         5229
Leu Cys Ile Asn Cys Tyr Asn Thr Lys Ser His Thr His Lys Met
    1730            1735                1740 gtg aag tgg ggg cta ggc cta gat gat gag ggc agc agt cag ggt         5274
Val Lys Trp Gly Leu Gly Leu Asp Asp Glu Gly Ser Ser Gln Gly
    1745            1750                1755 gag cca cag tcc aag agc ccc cag gaa tcc cgg cgt ctc agc atc         5319
Glu Pro Gln Ser Lys Ser Pro Gln Glu Ser Arg Arg Leu Ser Ile
    1760            1765                1770 cag cgc tgc atc cag tcc ctg gtg cat gcc tgc cag tgt cgc aat         5364
Gln Arg Cys Ile Gln Ser Leu Val His Ala Cys Gln Cys Arg Asn
    1775            1780                1785 gcc aac tgc tca ctg ccg tct tgc cag aag atg aag cga gtc gtg         5409
Ala Asn Cys Ser Leu Pro Ser Cys Gln Lys Met Lys Arg Val Val
    1790            1795                1800 cag cac acc aag ggc tgc aag cgc aag act aat gga gga tgc cca         5454
Gln His Thr Lys Gly Cys Lys Arg Lys Thr Asn Gly Gly Cys Pro
    1805            1810                1815 gtg tgc aag cag ctc att gct ctt tgc tgc tac cac gcc aaa cac         5499
Val Cys Lys Gln Leu Ile Ala Leu Cys Cys Tyr His Ala Lys His
    1820            1825                1830 tgc caa gaa aat aaa tgc cct gtg ccc ttc tgc ctc aac atc aaa         5544
Cys Gln Glu Asn Lys Cys Pro Val Pro Phe Cys Leu Asn Ile Lys
    1835            1840                1845 cat aac gtc cgc cag cag cag atc cag cac tgc ctg cag cag gct         5589
His Asn Val Arg Gln Gln Gln Ile Gln His Cys Leu Gln Gln Ala
    1850            1855                1860 cag ctc atg cgc cgg cga atg gca acc atg aac acc cgc aat gtg         5634
Gln Leu Met Arg Arg Arg Met Ala Thr Met Asn Thr Arg Asn Val
    1865            1870                1875 cct cag cag agt ttg cct tct cct acc tca gca cca ccc ggg act         5679
Pro Gln Gln Ser Leu Pro Ser Pro Thr Ser Ala Pro Pro Gly Thr
    1880            1885                1890
```

|                                                                                                     |      |
| --------------------------------------------------------------------------------------------------- | ---- |
| cct aca cag cag ccc agc aca ccc caa aca cca cag ccc cca gcc<br>Pro Thr Gln Gln Pro Ser Thr Pro Gln Thr Pro Gln Pro Pro Ala<br>    1895                1900                1905 | 5724 |
| cag cct cag cct tca cct gtt aac atg tca cca gca ggc ttc cct<br>Gln Pro Gln Pro Ser Pro Val Asn Met Ser Pro Ala Gly Phe Pro<br>    1910                1915                1920 | 5769 |
| aat gta gcc cgg act cag ccc cca aca ata gtg tct gct ggg aag<br>Asn Val Ala Arg Thr Gln Pro Pro Thr Ile Val Ser Ala Gly Lys<br>    1925                1930                1935 | 5814 |
| cct acc aac cag gtg cca gct ccc cca ccc cct gcc cag ccc cca<br>Pro Thr Asn Gln Val Pro Ala Pro Pro Pro Pro Ala Gln Pro Pro<br>    1940                1945                1950 | 5859 |
| cct gca gca gta gaa gca gcc cgg caa att gaa cgt gag gcc cag<br>Pro Ala Ala Val Glu Ala Ala Arg Gln Ile Glu Arg Glu Ala Gln<br>    1955                1960                1965 | 5904 |
| cag cag cag cac cta tac cga gca aac atc aac aat ggc atg ccc<br>Gln Gln Gln His Leu Tyr Arg Ala Asn Ile Asn Asn Gly Met Pro<br>    1970                1975                1980 | 5949 |
| cca gga cgt gac ggt atg ggg acc cca gga agc caa atg act cct<br>Pro Gly Arg Asp Gly Met Gly Thr Pro Gly Ser Gln Met Thr Pro<br>    1985                1990                1995 | 5994 |
| gtg ggc ctg aat gtg ccc cgt ccc aac caa gtc agt ggg cct gtc<br>Val Gly Leu Asn Val Pro Arg Pro Asn Gln Val Ser Gly Pro Val<br>    2000                2005                2010 | 6039 |
| atg tct agt atg cca cct ggg cag tgg cag cag gca ccc atc cct<br>Met Ser Ser Met Pro Pro Gly Gln Trp Gln Gln Ala Pro Ile Pro<br>    2015                2020                2025 | 6084 |
| cag cag cag ccg atg cca ggc atg ccc agg cct gta atg tcc atg<br>Gln Gln Gln Pro Met Pro Gly Met Pro Arg Pro Val Met Ser Met<br>    2030                2035                2040 | 6129 |
| cag gcc cag gca gca gtg gct ggg cca cgg atg ccc aat gtg cag<br>Gln Ala Gln Ala Ala Val Ala Gly Pro Arg Met Pro Asn Val Gln<br>    2045                2050                2055 | 6174 |
| cca aac agg agc atc tcg cca agt gcc ctg caa gac ctg cta cgg<br>Pro Asn Arg Ser Ile Ser Pro Ser Ala Leu Gln Asp Leu Leu Arg<br>    2060                2065                2070 | 6219 |
| acc cta aag tca ccc agc tct cct cag cag cag cag cag gtg ctg<br>Thr Leu Lys Ser Pro Ser Ser Pro Gln Gln Gln Gln Gln Val Leu<br>    2075                2080                2085 | 6264 |
| aac atc ctt aaa tca aac cca cag cta atg gca gct ttc atc aaa<br>Asn Ile Leu Lys Ser Asn Pro Gln Leu Met Ala Ala Phe Ile Lys<br>    2090                2095                2100 | 6309 |
| cag cgc aca gcc aag tat gtg gcc aat cag cct ggc atg cag ccc<br>Gln Arg Thr Ala Lys Tyr Val Ala Asn Gln Pro Gly Met Gln Pro<br>    2105                2110                2115 | 6354 |
| cag ccc gga ctt caa tcc cag cct ggt atg cag ccc cag cct ggc<br>Gln Pro Gly Leu Gln Ser Gln Pro Gly Met Gln Pro Gln Pro Gly<br>    2120                2125                2130 | 6399 |
| atg cac cag cag cct agt ttg caa aac ctg aac gca atg caa gct<br>Met His Gln Gln Pro Ser Leu Gln Asn Leu Asn Ala Met Gln Ala<br>    2135                2140                2145 | 6444 |
| ggt gtg cca cgg cct ggt gtg cct cca cca caa cca gca atg gga<br>Gly Val Pro Arg Pro Gly Val Pro Pro Pro Gln Pro Ala Met Gly<br>    2150                2155                2160 | 6489 |
| ggc ctg aat ccc cag gga caa gct ctg aac atc atg aac cca gga<br>Gly Leu Asn Pro Gln Gly Gln Ala Leu Asn Ile Met Asn Pro Gly<br>    2165                2170                2175 | 6534 |
| cac aac ccc aac atg aca aac atg aat cca cag tac cga gaa atg<br>His Asn Pro Asn Met Thr Asn Met Asn Pro Gln Tyr Arg Glu Met<br>    2180                2185                2190 | 6579 |

-continued

```
gtg agg aga cag ctg cta cag cac cag cag cag cag caa cag       6624
Val Arg Arg Gln Leu Leu Gln His Gln Gln Gln Gln Gln Gln
    2195                2200                2205 cag cag cag cag cag caa caa caa aat agt gcc agc ttg gcc ggg   6669
Gln Gln Gln Gln Gln Gln Gln Gln Asn Ser Ala Ser Leu Ala Gly
    2210                2215                2220 ggc atg gcg gga cac agc cag ttc cag cag cca caa gga cct gga   6714
Gly Met Ala Gly His Ser Gln Phe Gln Gln Pro Gln Gly Pro Gly
    2225                2230                2235 ggt tat gcc cca gcc atg cag cag caa cgc atg caa cag cac ctc   6759
Gly Tyr Ala Pro Ala Met Gln Gln Gln Arg Met Gln Gln His Leu
    2240                2245                2250 ccc atc cag ggc agc tcc atg ggc cag atg gct gct cca atg gga   6804
Pro Ile Gln Gly Ser Ser Met Gly Gln Met Ala Ala Pro Met Gly
    2255                2260                2265 caa ctt ggc cag atg ggg cag cct ggg cta ggg gca gac agc acc   6849
Gln Leu Gly Gln Met Gly Gln Pro Gly Leu Gly Ala Asp Ser Thr
    2270                2275                2280 cct aat atc cag cag gcc ctg cag caa cgg att ctg cag cag cag   6894
Pro Asn Ile Gln Gln Ala Leu Gln Gln Arg Ile Leu Gln Gln Gln
    2285                2290                2295 cag atg aag caa caa att ggg tca cca ggc cag ccg aac ccc atg   6939
Gln Met Lys Gln Gln Ile Gly Ser Pro Gly Gln Pro Asn Pro Met
    2300                2305                2310 agc ccc cag cag cac atg ctc tca gga cag cca cag gcc tca cat   6984
Ser Pro Gln Gln His Met Leu Ser Gly Gln Pro Gln Ala Ser His
    2315                2320                2325 ctc cct ggc cag cag atc gcc aca tcc ctt agt aac cag gtg cga   7029
Leu Pro Gly Gln Gln Ile Ala Thr Ser Leu Ser Asn Gln Val Arg
    2330                2335                2340 tct cca gcc cct gtg cag tct cca cgg ccc caa tcc caa cct cca   7074
Ser Pro Ala Pro Val Gln Ser Pro Arg Pro Gln Ser Gln Pro Pro
    2345                2350                2355 cat tcc agc ccg tca cca cgg ata caa ccc cag cct tca cca cac   7119
His Ser Ser Pro Ser Pro Arg Ile Gln Pro Gln Pro Ser Pro His
    2360                2365                2370 cat gtt tca ccc cag act gga acc cct cac cct gga ctc gca gtc   7164
His Val Ser Pro Gln Thr Gly Thr Pro His Pro Gly Leu Ala Val
    2375                2380                2385 acc atg gcc agc tcc atg gat cag gga cac ctg ggg aac cct gaa   7209
Thr Met Ala Ser Ser Met Asp Gln Gly His Leu Gly Asn Pro Glu
    2390                2395                2400 cag agt gca atg ctc ccc cag ctg aat acc ccc aac agg agc gca   7254
Gln Ser Ala Met Leu Pro Gln Leu Asn Thr Pro Asn Arg Ser Ala
    2405                2410                2415 ctg tcc agt gaa ctg tcc ctg gtt ggt gat acc acg gga gac aca   7299
Leu Ser Ser Glu Leu Ser Leu Val Gly Asp Thr Thr Gly Asp Thr
    2420                2425                2430 cta gaa aag ttt gtg gag ggt ttg tag                           7326
Leu Glu Lys Phe Val Glu Gly Leu
    2435                2440
```

<210> SEQ ID NO 8
<211> LENGTH: 2441
<212> TYPE: PRT
<213> ORGANISM: mouse

<400> SEQUENCE: 8

Met Ala Glu Asn Leu Leu Asp Gly Pro Pro Asn Pro Lys Arg Ala Lys
1               5                   10                  15

-continued

```
Leu Ser Ser Pro Gly Phe Ser Ala Asn Asp Asn Thr Asp Phe Gly Ser
             20                  25                  30

Leu Phe Asp Leu Glu Asn Asp Leu Pro Asp Glu Leu Ile Pro Asn Gly
         35                  40                  45

Glu Leu Ser Leu Leu Asn Ser Gly Asn Leu Val Pro Asp Ala Ala Ser
 50                      55                  60

Lys His Lys Gln Leu Ser Glu Leu Leu Arg Gly Ser Gly Ser Ser
 65                  70                  75                  80

Ile Asn Pro Gly Ile Gly Asn Val Ser Ala Ser Ser Pro Val Gln Gln
                 85                  90                  95

Gly Leu Gly Gly Gln Ala Gln Gly Gln Pro Asn Ser Thr Asn Met Ala
             100                 105                 110

Ser Leu Gly Ala Met Gly Lys Ser Pro Leu Asn Gln Gly Asp Ser Ser
         115                 120                 125

Thr Pro Asn Leu Pro Lys Gln Ala Ala Ser Thr Ser Gly Pro Thr Pro
     130                 135                 140

Pro Ala Ser Gln Ala Leu Asn Pro Gln Ala Gln Lys Gln Val Gly Leu
145                 150                 155                 160

Val Thr Ser Ser Pro Ala Thr Ser Gln Thr Gly Pro Gly Ile Cys Met
                 165                 170                 175

Asn Ala Asn Phe Asn Gln Thr His Pro Gly Leu Leu Asn Ser Asn Ser
             180                 185                 190

Gly His Ser Leu Met Asn Gln Ala Gln Gln Gly Gln Ala Gln Val Met
         195                 200                 205

Asn Gly Ser Leu Gly Ala Ala Gly Arg Gly Arg Gly Ala Gly Met Pro
     210                 215                 220

Tyr Pro Ala Pro Ala Met Gln Gly Ala Thr Ser Ser Val Leu Ala Glu
225                 230                 235                 240

Thr Leu Thr Gln Val Ser Pro Gln Met Ala Gly His Ala Gly Leu Asn
                 245                 250                 255

Thr Ala Gln Ala Gly Gly Met Thr Lys Met Gly Met Thr Gly Thr Thr
             260                 265                 270

Ser Pro Phe Gly Gln Pro Phe Ser Gln Thr Gly Gly Gln Gln Met Gly
         275                 280                 285

Ala Thr Gly Val Asn Pro Gln Leu Ala Ser Lys Gln Ser Met Val Asn
     290                 295                 300

Ser Leu Pro Ala Phe Pro Thr Asp Ile Lys Asn Thr Ser Val Thr Thr
305                 310                 315                 320

Val Pro Asn Met Ser Gln Leu Gln Thr Ser Val Gly Ile Val Pro Thr
                 325                 330                 335

Gln Ala Ile Ala Thr Gly Pro Thr Ala Asp Pro Glu Lys Arg Lys Leu
             340                 345                 350

Ile Gln Gln Gln Leu Val Leu Leu Leu His Ala His Lys Cys Gln Arg
         355                 360                 365

Arg Glu Gln Ala Asn Gly Glu Val Arg Ala Cys Ser Leu Pro His Cys
     370                 375                 380

Arg Thr Met Lys Asn Val Leu Asn His Met Thr His Cys Gln Ala Pro
385                 390                 395                 400

Lys Ala Cys Gln Val Ala His Cys Ala Ser Ser Arg Gln Ile Ile Ser
                 405                 410                 415

His Trp Lys Asn Cys Thr Arg His Asp Cys Pro Val Cys Leu Pro Leu
             420                 425                 430
```

```
Lys Asn Ala Ser Asp Lys Arg Asn Gln Gln Thr Ile Leu Gly Ser Pro
            435                 440                 445

Ala Ser Gly Ile Gln Asn Thr Ile Gly Ser Val Gly Ala Gly Gln Gln
        450                 455                 460

Asn Ala Thr Ser Leu Ser Asn Pro Asn Pro Ile Asp Pro Ser Ser Met
465                 470                 475                 480

Gln Arg Ala Tyr Ala Ala Leu Gly Leu Pro Tyr Met Asn Gln Pro Gln
                485                 490                 495

Thr Gln Leu Gln Pro Gln Val Pro Gly Gln Gln Pro Ala Gln Pro Pro
            500                 505                 510

Ala His Gln Gln Met Arg Thr Leu Asn Ala Leu Gly Asn Asn Pro Met
        515                 520                 525

Ser Val Pro Ala Gly Gly Ile Thr Thr Asp Gln Gln Pro Pro Asn Leu
    530                 535                 540

Ile Ser Glu Ser Ala Leu Pro Thr Ser Leu Gly Ala Thr Asn Pro Leu
545                 550                 555                 560

Met Asn Asp Gly Ser Asn Ser Gly Asn Ile Gly Ser Leu Ser Thr Ile
                565                 570                 575

Pro Thr Ala Ala Pro Pro Ser Ser Thr Gly Val Arg Lys Gly Trp His
            580                 585                 590

Glu His Val Thr Gln Asp Leu Arg Ser His Leu Val His Lys Leu Val
        595                 600                 605

Gln Ala Ile Phe Pro Thr Pro Asp Pro Ala Ala Leu Lys Asp Arg Arg
    610                 615                 620

Met Glu Asn Leu Val Ala Tyr Ala Lys Lys Val Glu Gly Asp Met Tyr
625                 630                 635                 640

Glu Ser Ala Asn Ser Arg Asp Glu Tyr Tyr His Leu Leu Ala Glu Lys
                645                 650                 655

Ile Tyr Lys Ile Gln Lys Glu Leu Glu Glu Lys Arg Arg Thr Arg Leu
            660                 665                 670

His Lys Gln Gly Ile Leu Gly Asn Gln Pro Ala Leu Pro Ala Ser Gly
        675                 680                 685

Ala Gln Pro Pro Val Ile Pro Pro Ala Gln Ser Val Arg Pro Pro Asn
    690                 695                 700

Gly Pro Leu Pro Leu Pro Val Asn Arg Met Gln Val Ser Gln Gly Met
705                 710                 715                 720

Asn Ser Phe Asn Pro Met Ser Leu Gly Asn Val Gln Leu Pro Gln Ala
                725                 730                 735

Pro Met Gly Pro Arg Ala Ala Ser Pro Met Asn His Ser Val Gln Met
            740                 745                 750

Asn Ser Met Ala Ser Val Pro Gly Met Ala Ile Ser Pro Ser Arg Met
        755                 760                 765

Pro Gln Pro Pro Asn Met Met Gly Thr His Ala Asn Asn Ile Met Ala
    770                 775                 780

Gln Ala Pro Thr Gln Asn Gln Phe Leu Pro Gln Asn Gln Phe Pro Ser
785                 790                 795                 800

Ser Ser Gly Ala Met Ser Val Asn Ser Val Gly Met Gly Gln Pro Ala
                805                 810                 815

Ala Gln Ala Gly Val Ser Gln Gly Gln Glu Pro Gly Ala Ala Leu Pro
            820                 825                 830

Asn Pro Leu Asn Met Leu Ala Pro Gln Ala Ser Gln Leu Pro Cys Pro
        835                 840                 845

Pro Val Thr Gln Ser Pro Leu His Pro Thr Pro Pro Ala Ser Thr
```

-continued

```
            850                 855                 860
Ala Ala Gly Met Pro Ser Leu Gln His Pro Thr Ala Pro Gly Met Thr
865                 870                 875                 880
Pro Pro Gln Pro Ala Ala Pro Thr Gln Pro Ser Thr Pro Val Ser Ser
                885                 890                 895
Gly Gln Thr Pro Thr Pro Thr Pro Gly Ser Val Pro Ser Ala Ala Gln
            900                 905                 910
Thr Gln Ser Thr Pro Thr Val Gln Ala Ala Gln Ala Gln Val Thr
            915                 920                 925
Pro Gln Pro Gln Thr Pro Val Gln Pro Pro Ser Val Ala Thr Pro Gln
930                 935                 940
Ser Ser Gln Gln Gln Pro Thr Pro Val His Thr Gln Pro Pro Gly Thr
945                 950                 955                 960
Pro Leu Ser Gln Ala Ala Ala Ser Ile Asp Asn Arg Val Pro Thr Pro
                965                 970                 975
Ser Thr Val Thr Ser Ala Glu Thr Ser Ser Gln Gln Pro Gly Pro Asp
            980                 985                 990
Val Pro Met Leu Glu Met Lys Thr Glu Val Gln Thr Asp Asp Ala Glu
            995                1000                1005
Pro Glu Pro Thr Glu Ser Lys Gly Glu Pro Arg Ser Glu Met Met
1010                1015                1020
Glu Glu Asp Leu Gln Gly Ser Ser Gln Val Lys Glu Glu Thr Asp
1025                1030                1035
Thr Thr Glu Gln Lys Ser Glu Pro Met Glu Val Glu Glu Lys Lys
1040                1045                1050
Pro Glu Val Lys Val Glu Ala Lys Glu Glu Glu Asn Ser Ser
1055                1060                1065
Asn Asp Thr Ala Ser Gln Ser Thr Ser Pro Ser Gln Pro Arg Lys
1070                1075                1080
Lys Ile Phe Lys Pro Glu Glu Leu Arg Gln Ala Leu Met Pro Thr
1085                1090                1095
Leu Glu Ala Leu Tyr Arg Gln Asp Pro Glu Ser Leu Pro Phe Arg
1100                1105                1110
Gln Pro Val Asp Pro Gln Leu Leu Gly Ile Pro Asp Tyr Phe Asp
1115                1120                1125
Ile Val Lys Asn Pro Met Asp Leu Ser Thr Ile Lys Arg Lys Leu
1130                1135                1140
Asp Thr Gly Gln Tyr Gln Glu Pro Trp Gln Tyr Val Asp Asp Val
1145                1150                1155
Arg Leu Met Phe Asn Asn Ala Trp Leu Tyr Asn Arg Lys Thr Ser
1160                1165                1170
Arg Val Tyr Lys Phe Cys Ser Lys Leu Ala Glu Val Phe Glu Gln
1175                1180                1185
Glu Ile Asp Pro Val Met Gln Ser Leu Gly Tyr Cys Cys Gly Arg
1190                1195                1200
Lys Tyr Glu Phe Ser Pro Gln Thr Leu Cys Cys Tyr Gly Lys Gln
1205                1210                1215
Leu Cys Thr Ile Pro Arg Asp Ala Ala Tyr Tyr Ser Tyr Gln Asn
1220                1225                1230
Arg Tyr His Phe Cys Gly Lys Cys Phe Thr Glu Ile Gln Gly Glu
1235                1240                1245
Asn Val Thr Leu Gly Asp Asp Pro Ser Gln Pro Gln Thr Thr Ile
1250                1255                1260
```

-continued

```
Ser Lys Asp Gln Phe Glu Lys Lys Asn Asp Thr Leu Asp Pro
1265                1270                1275

Glu Pro Phe Val Asp Cys Lys Glu Cys Gly Arg Lys Met His Gln
1280                1285                1290

Ile Cys Val Leu His Tyr Asp Ile Ile Trp Pro Ser Gly Phe Val
1295                1300                1305

Cys Asp Asn Cys Leu Lys Lys Thr Gly Arg Pro Arg Lys Glu Asn
1310                1315                1320

Lys Phe Ser Ala Lys Arg Leu Gln Thr Thr Arg Leu Gly Asn His
1325                1330                1335

Leu Glu Asp Arg Val Asn Lys Phe Leu Arg Arg Gln Asn His Pro
1340                1345                1350

Glu Ala Gly Glu Val Phe Val Arg Val Val Ala Ser Ser Asp Lys
1355                1360                1365

Thr Val Glu Val Lys Pro Gly Met Lys Ser Arg Phe Val Asp Ser
1370                1375                1380

Gly Glu Met Ser Glu Ser Phe Pro Tyr Arg Thr Lys Ala Leu Phe
1385                1390                1395

Ala Phe Glu Glu Ile Asp Gly Val Asp Val Cys Phe Phe Gly Met
1400                1405                1410

His Val Gln Asp Thr Ala Leu Ile Ala Pro His Gln Ile Gln Gly
1415                1420                1425

Cys Val Tyr Ile Ser Tyr Leu Asp Ser Ile His Phe Phe Arg Pro
1430                1435                1440

Arg Cys Leu Arg Thr Ala Val Tyr His Glu Ile Leu Ile Gly Tyr
1445                1450                1455

Leu Glu Tyr Val Lys Lys Leu Val Tyr Val Thr Ala His Ile Trp
1460                1465                1470

Ala Cys Pro Pro Ser Glu Gly Asp Asp Tyr Ile Phe His Cys His
1475                1480                1485

Pro Pro Asp Gln Lys Ile Pro Lys Pro Lys Arg Leu Gln Glu Trp
1490                1495                1500

Tyr Lys Lys Met Leu Asp Lys Ala Phe Ala Glu Arg Ile Ile Asn
1505                1510                1515

Asp Tyr Lys Asp Ile Phe Lys Gln Ala Asn Glu Asp Arg Leu Thr
1520                1525                1530

Ser Ala Lys Glu Leu Pro Tyr Phe Glu Gly Asp Phe Trp Pro Asn
1535                1540                1545

Val Leu Glu Glu Ser Ile Lys Glu Leu Glu Gln Glu Glu Glu Glu
1550                1555                1560

Arg Lys Lys Glu Glu Ser Thr Ala Ala Ser Glu Thr Pro Glu Gly
1565                1570                1575

Ser Gln Gly Asp Ser Lys Asn Ala Lys Lys Lys Asn Asn Lys Lys
1580                1585                1590

Thr Asn Lys Asn Lys Ser Ser Ile Ser Arg Ala Asn Lys Lys Lys
1595                1600                1605

Pro Ser Met Pro Asn Val Ser Asn Asp Leu Ser Gln Lys Leu Tyr
1610                1615                1620

Ala Thr Met Glu Lys His Lys Glu Val Phe Phe Val Ile His Leu
1625                1630                1635

His Ala Gly Pro Val Ile Ser Thr Gln Pro Pro Ile Val Asp Pro
1640                1645                1650
```

-continued

```
Asp Pro Leu Leu Ser Cys Asp Leu Met Asp Gly Arg Asp Ala Phe
    1655                1660                1665

Leu Thr Leu Ala Arg Asp Lys His Trp Glu Phe Ser Ser Leu Arg
    1670                1675                1680

Arg Ser Lys Trp Ser Thr Leu Cys Met Leu Val Glu Leu His Thr
    1685                1690                1695

Gln Gly Gln Asp Arg Phe Val Tyr Thr Cys Asn Glu Cys Lys His
    1700                1705                1710

His Val Glu Thr Arg Trp His Cys Thr Val Cys Glu Asp Tyr Asp
    1715                1720                1725

Leu Cys Ile Asn Cys Tyr Asn Thr Lys Ser His Thr His Lys Met
    1730                1735                1740

Val Lys Trp Gly Leu Gly Leu Asp Asp Glu Gly Ser Ser Gln Gly
    1745                1750                1755

Glu Pro Gln Ser Lys Ser Pro Gln Glu Ser Arg Arg Leu Ser Ile
    1760                1765                1770

Gln Arg Cys Ile Gln Ser Leu Val His Ala Cys Gln Cys Arg Asn
    1775                1780                1785

Ala Asn Cys Ser Leu Pro Ser Cys Gln Lys Met Lys Arg Val Val
    1790                1795                1800

Gln His Thr Lys Gly Cys Lys Arg Lys Thr Asn Gly Gly Cys Pro
    1805                1810                1815

Val Cys Lys Gln Leu Ile Ala Leu Cys Cys Tyr His Ala Lys His
    1820                1825                1830

Cys Gln Glu Asn Lys Cys Pro Val Pro Phe Cys Leu Asn Ile Lys
    1835                1840                1845

His Asn Val Arg Gln Gln Ile Gln His Cys Leu Gln Gln Ala
    1850                1855                1860

Gln Leu Met Arg Arg Arg Met Ala Thr Met Asn Thr Arg Asn Val
    1865                1870                1875

Pro Gln Gln Ser Leu Pro Ser Pro Thr Ser Ala Pro Pro Gly Thr
    1880                1885                1890

Pro Thr Gln Gln Pro Ser Thr Pro Gln Thr Pro Gln Pro Pro Ala
    1895                1900                1905

Gln Pro Gln Pro Ser Pro Val Asn Met Ser Pro Ala Gly Phe Pro
    1910                1915                1920

Asn Val Ala Arg Thr Gln Pro Pro Thr Ile Val Ser Ala Gly Lys
    1925                1930                1935

Pro Thr Asn Gln Val Pro Ala Pro Pro Pro Ala Gln Pro Pro
    1940                1945                1950

Pro Ala Ala Val Glu Ala Ala Arg Gln Ile Glu Arg Glu Ala Gln
    1955                1960                1965

Gln Gln Gln His Leu Tyr Arg Ala Asn Ile Asn Asn Gly Met Pro
    1970                1975                1980

Pro Gly Arg Asp Gly Met Gly Thr Pro Gly Ser Gln Met Thr Pro
    1985                1990                1995

Val Gly Leu Asn Val Pro Arg Pro Asn Gln Val Ser Gly Pro Val
    2000                2005                2010

Met Ser Ser Met Pro Pro Gly Gln Trp Gln Gln Ala Pro Ile Pro
    2015                2020                2025

Gln Gln Gln Pro Met Pro Gly Met Pro Arg Pro Val Met Ser Met
    2030                2035                2040

Gln Ala Gln Ala Ala Val Ala Gly Pro Arg Met Pro Asn Val Gln
```

-continued

```
              2045                2050                2055
Pro  Asn  Arg  Ser  Ile  Ser  Pro  Ser  Ala  Leu  Gln  Asp  Leu  Leu  Arg
         2060                2065                2070

Thr  Leu  Lys  Ser  Pro  Ser  Ser  Pro  Gln  Gln  Gln  Gln  Gln  Val  Leu
    2075                2080                2085

Asn  Ile  Leu  Lys  Ser  Asn  Pro  Gln  Leu  Met  Ala  Ala  Phe  Ile  Lys
    2090                2095                2100

Gln  Arg  Thr  Ala  Lys  Tyr  Val  Ala  Asn  Gln  Pro  Gly  Met  Gln  Pro
    2105                2110                2115

Gln  Pro  Gly  Leu  Gln  Ser  Gln  Pro  Gly  Met  Gln  Pro  Gln  Pro  Gly
    2120                2125                2130

Met  His  Gln  Gln  Pro  Ser  Leu  Gln  Asn  Leu  Asn  Ala  Met  Gln  Ala
    2135                2140                2145

Gly  Val  Pro  Arg  Pro  Gly  Val  Pro  Pro  Gln  Pro  Ala  Met  Gly
    2150                2155                2160

Gly  Leu  Asn  Pro  Gln  Gly  Gln  Ala  Leu  Asn  Ile  Met  Asn  Pro  Gly
    2165                2170                2175

His  Asn  Pro  Asn  Met  Thr  Asn  Met  Asn  Pro  Gln  Tyr  Arg  Glu  Met
    2180                2185                2190

Val  Arg  Arg  Gln  Leu  Leu  Gln  His  Gln  Gln  Gln  Gln  Gln  Gln  Gln
    2195                2200                2205

Gln  Gln  Gln  Gln  Gln  Gln  Gln  Asn  Ser  Ala  Ser  Leu  Ala  Gly
    2210                2215                2220

Gly  Met  Ala  Gly  His  Ser  Gln  Phe  Gln  Pro  Gln  Gly  Pro  Gly
    2225                2230                2235

Gly  Tyr  Ala  Pro  Ala  Met  Gln  Gln  Gln  Arg  Met  Gln  Gln  His  Leu
    2240                2245                2250

Pro  Ile  Gln  Gly  Ser  Ser  Met  Gly  Gln  Met  Ala  Ala  Pro  Met  Gly
    2255                2260                2265

Gln  Leu  Gly  Gln  Met  Gly  Gln  Pro  Gly  Leu  Gly  Ala  Asp  Ser  Thr
    2270                2275                2280

Pro  Asn  Ile  Gln  Gln  Ala  Leu  Gln  Gln  Arg  Ile  Leu  Gln  Gln  Gln
    2285                2290                2295

Gln  Met  Lys  Gln  Gln  Ile  Gly  Ser  Pro  Gly  Gln  Pro  Asn  Pro  Met
    2300                2305                2310

Ser  Pro  Gln  Gln  His  Met  Leu  Ser  Gly  Gln  Pro  Gln  Ala  Ser  His
    2315                2320                2325

Leu  Pro  Gly  Gln  Gln  Ile  Ala  Thr  Ser  Leu  Ser  Asn  Gln  Val  Arg
    2330                2335                2340

Ser  Pro  Ala  Pro  Val  Gln  Ser  Pro  Arg  Pro  Gln  Ser  Gln  Pro  Pro
    2345                2350                2355

His  Ser  Ser  Pro  Ser  Pro  Arg  Ile  Gln  Pro  Gln  Pro  Ser  Pro  His
    2360                2365                2370

His  Val  Ser  Pro  Gln  Thr  Gly  Thr  Pro  His  Pro  Gly  Leu  Ala  Val
    2375                2380                2385

Thr  Met  Ala  Ser  Ser  Met  Asp  Gln  Gly  His  Leu  Gly  Asn  Pro  Glu
    2390                2395                2400

Gln  Ser  Ala  Met  Leu  Pro  Gln  Leu  Asn  Thr  Pro  Asn  Arg  Ser  Ala
    2405                2410                2415

Leu  Ser  Ser  Glu  Leu  Ser  Leu  Val  Gly  Asp  Thr  Thr  Gly  Asp  Thr
    2420                2425                2430

Leu  Glu  Lys  Phe  Val  Glu  Gly  Leu
    2435                2440
```

<210> SEQ ID NO 9
<211> LENGTH: 8147
<212> TYPE: DNA
<213> ORGANISM: human
<220> FEATURE:
<221> NAME/KEY: CDS
<222> LOCATION: (819)..(8147)

<400> SEQUENCE: 9

```
tccgaattcc ttttttttaa ttgaggaatc aacagccgcc atcttgtcgc ggacccgacc      60
ggggcttcga gcgcgatcta ctcggccccg ccggtcccgg gccccacaac cgcccgcgca     120
ccccgctccg cccggccggc ccgctccgcc cggccctcgg cgcccgcccc ggcggccccg     180
ctcgcctctc ggctcggcct cccggagccc ggcggcggcg gcggcggcag cggcggcggc     240
ggcggcggaa cggggggtgg ggggggccgcg gcggcggcgg cgaccccgct cggcgcattg     300
tttttcctca cggcggcggc ggcggcgggc cgcgggccgg gagcggagcc cggagccccc     360
tcgtcgtcgg gccgcgagcg aattcattaa gtgggggcgcg ggggggggagc gaggcggcgg     420
cggcggcggc accatgttct cggggactgc ctgagccgcc cggccgggcg ccgtcgctgc     480
cagccgggcc cggggggggcg gccgggccgc cggggcgccc ccaccgcgga gtgtcgcgct     540
cgggaggcgg gcaggggatg aggggccgc ggccggcgg ggcggcggcg gccggggggcg     600
ggcggtgagc gctgcgggc gctgttgctg tggctgagat ttggccgccg cctcccccac     660
ccggcctgcg ccctccctct ccctcggcgc ccgcccgcgc cgctcgcggc gcccgcgctc     720
gctcctctcc ctcgcagccg gcagggcccc cgacccccgt ccgggccctc gccggcccgg     780
ccgcccgtgc ccggggctgt tttcgcgagc aggtgaaa atg gct gag aac ttg ctg     836
                                        Met Ala Glu Asn Leu Leu
                                          1               5
gac gga ccg ccc aac ccc aaa aga gcc aaa ctc agc tcg ccc ggt ttc        884
Asp Gly Pro Pro Asn Pro Lys Arg Ala Lys Leu Ser Ser Pro Gly Phe
         10                  15                  20
tcg gcg aat gac agc aca gat ttt gga tca ttg ttt gac ttg gaa aat        932
Ser Ala Asn Asp Ser Thr Asp Phe Gly Ser Leu Phe Asp Leu Glu Asn
     25                  30                  35
gat ctt cct gat gag ctg ata ccc aat gga gga gaa tta ggc ctt tta        980
Asp Leu Pro Asp Glu Leu Ile Pro Asn Gly Gly Glu Leu Gly Leu Leu
 40                  45                  50
aac agt ggg aac ctt gtt cca gat gct gct tcc aaa cat aaa caa ctg       1028
Asn Ser Gly Asn Leu Val Pro Asp Ala Ala Ser Lys His Lys Gln Leu
55                  60                  65                  70
tcg gag ctt cta cga gga ggc agc ggc tct agt atc aac cca gga ata       1076
Ser Glu Leu Leu Arg Gly Gly Ser Gly Ser Ser Ile Asn Pro Gly Ile
                 75                  80                  85
gga aat gtg agc gcc agc agc ccc gtg cag cag ggc ctg ggt ggc cag       1124
Gly Asn Val Ser Ala Ser Ser Pro Val Gln Gln Gly Leu Gly Gly Gln
             90                  95                 100
gct caa ggg cag ccg aac agt gct aac atg gcc agc ctc agt gcc atg       1172
Ala Gln Gly Gln Pro Asn Ser Ala Asn Met Ala Ser Leu Ser Ala Met
         105                 110                 115
ggc aag agc cct ctg agc cag gga gat tct tca gcc ccc agc ctg cct       1220
Gly Lys Ser Pro Leu Ser Gln Gly Asp Ser Ser Ala Pro Ser Leu Pro
     120                 125                 130
aaa cag gca gcc agc acc tct ggg ccc acc ccc gct gcc tcc caa gca       1268
Lys Gln Ala Ala Ser Thr Ser Gly Pro Thr Pro Ala Ala Ser Gln Ala
135                 140                 145                 150
ctg aat ccg caa gca caa aag caa gtg ggg ctg gcg act agc agc cct       1316
```

```
              Leu Asn Pro Gln Ala Gln Lys Gln Val Gly Leu Ala Thr Ser Ser Pro
                              155                 160                 165 gcc acg tca cag act gga cct ggt atc tgc atg aat gct aac ttt aac       1364
Ala Thr Ser Gln Thr Gly Pro Gly Ile Cys Met Asn Ala Asn Phe Asn
            170                 175                 180 cag acc cac cca ggc ctc ctc aat agt aac tct ggc agc tta att           1412
Gln Thr His Pro Gly Leu Leu Asn Ser Asn Ser Gly His Ser Leu Ile
            185                 190                 195 aat cag gct tca caa ggg cag gcg caa gtc atg aat gga tct ctt ggg       1460
Asn Gln Ala Ser Gln Gly Gln Ala Gln Val Met Asn Gly Ser Leu Gly
            200                 205                 210 gct gct ggc aga gga agg gga gct gga atg ccg tac cct act cca gcc       1508
Ala Ala Gly Arg Gly Arg Gly Ala Gly Met Pro Tyr Pro Thr Pro Ala
215                 220                 225                 230 atg cag ggc gcc tcg agc agc gtg ctg gct gag acc cta acg cag gtt       1556
Met Gln Gly Ala Ser Ser Ser Val Leu Ala Glu Thr Leu Thr Gln Val
                235                 240                 245 tcc ccg caa atg act ggt cac gcg gga ctg aac acc gca cag gca gga       1604
Ser Pro Gln Met Thr Gly His Ala Gly Leu Asn Thr Ala Gln Ala Gly
            250                 255                 260 ggc atg gcc aag atg gga ata act ggg aac aca agt cca ttt gga cag       1652
Gly Met Ala Lys Met Gly Ile Thr Gly Asn Thr Ser Pro Phe Gly Gln
            265                 270                 275 ccc ttt agt caa gct gga ggg cag cca atg gga gcc act gga gtg aac       1700
Pro Phe Ser Gln Ala Gly Gly Gln Pro Met Gly Ala Thr Gly Val Asn
            280                 285                 290 ccc cag tta gcc agc aaa cag agc atg gtc aac agt ttg ccc acc ttc       1748
Pro Gln Leu Ala Ser Lys Gln Ser Met Val Asn Ser Leu Pro Thr Phe
295                 300                 305                 310 cct aca gat atc aag aat act tca gtc acc aac gtg cca aat atg tct       1796
Pro Thr Asp Ile Lys Asn Thr Ser Val Thr Asn Val Pro Asn Met Ser
            315                 320                 325 cag atg caa aca tca gtg gga att gta ccc aca caa gca att gca aca       1844
Gln Met Gln Thr Ser Val Gly Ile Val Pro Thr Gln Ala Ile Ala Thr
            330                 335                 340 ggc ccc act gca gat cct gaa aaa cgc aaa ctg ata cag cag cag ctg       1892
Gly Pro Thr Ala Asp Pro Glu Lys Arg Lys Leu Ile Gln Gln Gln Leu
            345                 350                 355 gtt cta ctg ctt cat gct cat aag tgt cag aga cga gag caa gca aac       1940
Val Leu Leu Leu His Ala His Lys Cys Gln Arg Arg Glu Gln Ala Asn
            360                 365                 370 gga gag gtt cgg gcc tgc tcg ctc ccg cat tgt cga acc atg aaa aac       1988
Gly Glu Val Arg Ala Cys Ser Leu Pro His Cys Arg Thr Met Lys Asn
375                 380                 385                 390 gtt ttg aat cac atg acg cat tgt cag gct ggg aaa gcc tgc caa gtt       2036
Val Leu Asn His Met Thr His Cys Gln Ala Gly Lys Ala Cys Gln Val
            395                 400                 405 gcc cat tgt gca tct tca cga caa atc atc tct cat tgg aag aac tgc       2084
Ala His Cys Ala Ser Ser Arg Gln Ile Ile Ser His Trp Lys Asn Cys
            410                 415                 420 aca cga cat gac tgt cct gtt tgc ctc cct ttg aaa aat gcc agt gac       2132
Thr Arg His Asp Cys Pro Val Cys Leu Pro Leu Lys Asn Ala Ser Asp
            425                 430                 435 aag cga aac caa caa acc atc ctg ggg tct cca gct agt gga att caa       2180
Lys Arg Asn Gln Gln Thr Ile Leu Gly Ser Pro Ala Ser Gly Ile Gln
            440                 445                 450 aac aca att ggt tct gtt ggc aca ggg caa cag aat gcc act tct tta       2228
Asn Thr Ile Gly Ser Val Gly Thr Gly Gln Gln Asn Ala Thr Ser Leu
455                 460                 465                 470
```

| | |
|---|---|
| agt aac cca aat ccc ata gac ccc agc tcc atg cag cga gcc tat gct<br>Ser Asn Pro Asn Pro Ile Asp Pro Ser Ser Met Gln Arg Ala Tyr Ala<br>                         475                            480                         485 | 2276 |
| gct ctc gga ctc ccc tac atg aac cag ccc cag acg cag ctg cag cct<br>Ala Leu Gly Leu Pro Tyr Met Asn Gln Pro Gln Thr Gln Leu Gln Pro<br>                   490                           495                           500 | 2324 |
| cag gtt cct ggc cag caa cca gca cag cct caa acc cac cag cag atg<br>Gln Val Pro Gly Gln Gln Pro Ala Gln Pro Gln Thr His Gln Gln Met<br>      505                           510                           515 | 2372 |
| agg act ctc aac ccc ctg gga aat aat cca atg aac att cca gca gga<br>Arg Thr Leu Asn Pro Leu Gly Asn Asn Pro Met Asn Ile Pro Ala Gly<br>520                          525                           530 | 2420 |
| gga ata aca aca gat cag cag ccc cca aac ttg att tca gaa tca gct<br>Gly Ile Thr Thr Asp Gln Gln Pro Pro Asn Leu Ile Ser Glu Ser Ala<br>535                          540                         545                      550 | 2468 |
| ctt ccg act tcc ctg ggg gcc aca aac cca ctg atg aac gat ggc tcc<br>Leu Pro Thr Ser Leu Gly Ala Thr Asn Pro Leu Met Asn Asp Gly Ser<br>                   555                           560                         565 | 2516 |
| aac tct ggt aac att gga acc ctc agc act ata cca aca gca gct cct<br>Asn Ser Gly Asn Ile Gly Thr Leu Ser Thr Ile Pro Thr Ala Ala Pro<br>      570                           575                           580 | 2564 |
| cct tct agc acc ggt gta agg aaa ggc tgg cac gaa cat gtc act cag<br>Pro Ser Ser Thr Gly Val Arg Lys Gly Trp His Glu His Val Thr Gln<br>                 585                          590                       595 | 2612 |
| gac ctg cgg agc cat cta gtg cat aaa ctc gtc caa gcc atc ttc cca<br>Asp Leu Arg Ser His Leu Val His Lys Leu Val Gln Ala Ile Phe Pro<br>600                          605                           610 | 2660 |
| aca cct gat ccc gca gct cta aag gat cgc cgc atg gaa aac ctg gta<br>Thr Pro Asp Pro Ala Ala Leu Lys Asp Arg Arg Met Glu Asn Leu Val<br>615                          620                         625                      630 | 2708 |
| gcc tat gct aag aaa gtg gaa ggg gac atg tac gag tct gcc aac agc<br>Ala Tyr Ala Lys Lys Val Glu Gly Asp Met Tyr Glu Ser Ala Asn Ser<br>                   635                           640                         645 | 2756 |
| agg gat gaa tat tat cac tta tta gca gag aaa atc tac aag ata caa<br>Arg Asp Glu Tyr Tyr His Leu Leu Ala Glu Lys Ile Tyr Lys Ile Gln<br>      650                           655                           660 | 2804 |
| aaa gaa cta gaa gaa aaa cgg agg tcg cgt tta cat aaa caa ggc atc<br>Lys Glu Leu Glu Glu Lys Arg Arg Ser Arg Leu His Lys Gln Gly Ile<br>                   665                          670                       675 | 2852 |
| ttg ggg aac cag cca gcc tta cca gcc ccg ggg gct cag ccc cct gtg<br>Leu Gly Asn Gln Pro Ala Leu Pro Ala Pro Gly Ala Gln Pro Pro Val<br>680                          685                         690 | 2900 |
| att cca cag gca caa cct gtg aga cct cca aat gga ccc ctg tcc ctg<br>Ile Pro Gln Ala Gln Pro Val Arg Pro Pro Asn Gly Pro Leu Ser Leu<br>695                          700                         705                      710 | 2948 |
| cca gtg aat cgc atg caa gtt tct caa ggg atg aat tca ttt aac ccc<br>Pro Val Asn Arg Met Gln Val Ser Gln Gly Met Asn Ser Phe Asn Pro<br>                   715                          720                       725 | 2996 |
| atg tcc ttg ggg aac gtc cag ttg cca caa gca ccc atg gga cct cgt<br>Met Ser Leu Gly Asn Val Gln Leu Pro Gln Ala Pro Met Gly Pro Arg<br>730                          735                         740 | 3044 |
| gca gcc tcc cca atg aac cac tct gtc cag atg aac agc atg ggc tca<br>Ala Ala Ser Pro Met Asn His Ser Val Gln Met Asn Ser Met Gly Ser<br>               745                         750                       755 | 3092 |
| gtg cca ggg atg gcc att tct cct tcc cga atg cct cag cct ccg aac<br>Val Pro Gly Met Ala Ile Ser Pro Ser Arg Met Pro Gln Pro Pro Asn<br>760                          765                         770 | 3140 |
| atg atg ggt gca cac acc aac aac atg atg gcc cag gcg ccc gct cag<br>Met Met Gly Ala His Thr Asn Asn Met Met Ala Gln Ala Pro Ala Gln<br>775                          780                         785                      790 | 3188 |

```
agc cag ttt ctg cca cag aac cag ttc ccg tca tcc agc ggg gcg atg    3236
Ser Gln Phe Leu Pro Gln Asn Gln Phe Pro Ser Ser Ser Gly Ala Met
                795                 800                 805 agt gtg ggc atg ggg cag ccg cca gcc caa aca ggc gtg tca cag gga    3284
Ser Val Gly Met Gly Gln Pro Pro Ala Gln Thr Gly Val Ser Gln Gly
            810                 815                 820 cag gtg cct ggt gct gct ctt cct aac cct ctc aac atg ctg ggg cct    3332
Gln Val Pro Gly Ala Ala Leu Pro Asn Pro Leu Asn Met Leu Gly Pro
        825                 830                 835 cag gcc agc cag cta cct tgc cct cca gtg aca cag tca cca ctg cac    3380
Gln Ala Ser Gln Leu Pro Cys Pro Pro Val Thr Gln Ser Pro Leu His
    840                 845                 850 cca aca ccg cct cct gct tcc acg gct gct ggc atg cca tct ctc cag    3428
Pro Thr Pro Pro Pro Ala Ser Thr Ala Ala Gly Met Pro Ser Leu Gln
855                 860                 865                 870 cac acg aca cca cct ggg atg act cct ccc cag cca gca gct ccc act    3476
His Thr Thr Pro Pro Gly Met Thr Pro Pro Gln Pro Ala Ala Pro Thr
                875                 880                 885 cag cca tca act cct gtg tcg tct tcc ggg cag act ccc acc ccg act    3524
Gln Pro Ser Thr Pro Val Ser Ser Ser Gly Gln Thr Pro Thr Pro Thr
            890                 895                 900 cct ggc tca gtg ccc agt gct acc caa acc cag agc acc cct aca gtc    3572
Pro Gly Ser Val Pro Ser Ala Thr Gln Thr Gln Ser Thr Pro Thr Val
        905                 910                 915 cag gca gca gcc cag gcc cag gtg acc ccg cag cct caa acc cca gtt    3620
Gln Ala Ala Ala Gln Ala Gln Val Thr Pro Gln Pro Gln Thr Pro Val
    920                 925                 930 cag ccc ccg tct gtg gct acc cct cag tca tcg cag caa cag ccg acg    3668
Gln Pro Pro Ser Val Ala Thr Pro Gln Ser Ser Gln Gln Gln Pro Thr
935                 940                 945                 950 cct gtg cac gcc cag cct cct ggc aca ccg ctt tcc cag gca gca gcc    3716
Pro Val His Ala Gln Pro Pro Gly Thr Pro Leu Ser Gln Ala Ala Ala
                955                 960                 965 agc att gat aac aga gtc cct acc ccc tcc tcg gtg gcc agc gca gaa    3764
Ser Ile Asp Asn Arg Val Pro Thr Pro Ser Ser Val Ala Ser Ala Glu
            970                 975                 980 acc aat tcc cag cag cca gga cct gac gta cct gtg ctg gaa atg aag    3812
Thr Asn Ser Gln Gln Pro Gly Pro Asp Val Pro Val Leu Glu Met Lys
        985                 990                 995 acg gag    acc caa gca gag gac    act gag ccc gat cct    ggt gaa tcc    3857
Thr Glu    Thr Gln Ala Glu Asp    Thr Glu Pro Asp Pro    Gly Glu Ser
1000                1005                    1010 aaa ggg gag ccc agg tct gag    atg atg gag gag gat    ttg caa gga        3902
Lys Gly Glu Pro Arg Ser Glu    Met Met Glu Glu Asp    Leu Gln Gly
1015                    1020                    1025 gct tcc caa gtt aaa gaa gaa    aca gac ata gca gag    cag aaa tca        3947
Ala Ser Gln Val Lys Glu Glu    Thr Asp Ile Ala Glu    Gln Lys Ser
1030                    1035                    1040 gaa cca atg gaa gtg gat gaa    aag aaa cct gaa gtg    aaa gta gaa        3992
Glu Pro Met Glu Val Asp Glu    Lys Lys Pro Glu Val    Lys Val Glu
1045                    1050                    1055 gtt aaa gag gaa gaa gag agt    agc agt aac ggc aca    gcc tct cag        4037
Val Lys Glu Glu Glu Glu Ser    Ser Ser Asn Gly Thr    Ala Ser Gln
1060                    1065                    1070 tca aca tct cct tcg cag ccg    cgc aaa aaa atc ttt    aaa cca gag        4082
Ser Thr Ser Pro Ser Gln Pro    Arg Lys Lys Ile Phe    Lys Pro Glu
1075                    1080                    1085 gag tta cgc cag gcc ctc atg    cca acc cta gaa gca    ctg tat cga        4127
Glu Leu Arg Gln Ala Leu Met    Pro Thr Leu Glu Ala    Leu Tyr Arg
```

-continued

| | | | | | | | | | | |
|---|---|---|---|---|---|---|---|---|---|---|
| | 1090 | | | 1095 | | | 1100 | | | |
| cag | gac | cca | gag | tca | tta | cct | ttc | cgg | cag | cct | gta | gat | ccc | cag | 4172 |
| Gln | Asp | Pro | Glu | Ser | Leu | Pro | Phe | Arg | Gln | Pro | Val | Asp | Pro | Gln | |
| 1105 | | | | 1110 | | | | 1115 | | | | | | | | ctc ctc gga att cca gac tat ttt gac atc gta aag aat ccc atg    4217
Leu Leu Gly Ile Pro Asp Tyr Phe Asp Ile Val Lys Asn Pro Met
1120            1125            1130 gac ctc tcc acc atc aag cgg aag ctg gac aca ggg caa tac caa    4262
Asp Leu Ser Thr Ile Lys Arg Lys Leu Asp Thr Gly Gln Tyr Gln
1135            1140            1145 gag ccc tgg cag tac gtg gac gac gtc tgg ctc atg ttc aac aat    4307
Glu Pro Trp Gln Tyr Val Asp Asp Val Trp Leu Met Phe Asn Asn
1150            1155            1160 gcc tgg ctc tat aat cgc aag aca tcc cga gtc tat aag ttt tgc    4352
Ala Trp Leu Tyr Asn Arg Lys Thr Ser Arg Val Tyr Lys Phe Cys
1165            1170            1175 agt aag ctt gca gag gtc ttt gag cag gaa att gac cct gtc atg    4397
Ser Lys Leu Ala Glu Val Phe Glu Gln Glu Ile Asp Pro Val Met
1180            1185            1190 cag tcc ctt gga tat tgc tgt gga cgc aag tat gag ttt tcc cca    4442
Gln Ser Leu Gly Tyr Cys Cys Gly Arg Lys Tyr Glu Phe Ser Pro
1195            1200            1205 cag act ttg tgc tgc tat ggg aag cag ctg tgt acc att cct cgc    4487
Gln Thr Leu Cys Cys Tyr Gly Lys Gln Leu Cys Thr Ile Pro Arg
1210            1215            1220 gat gct gcc tac tac agc tat cag aat agg tat cat ttc tgt gag    4532
Asp Ala Ala Tyr Tyr Ser Tyr Gln Asn Arg Tyr His Phe Cys Glu
1225            1230            1235 aag tgt ttc aca gag atc cag ggc gag aat gtg acc ctg ggt gac    4577
Lys Cys Phe Thr Glu Ile Gln Gly Glu Asn Val Thr Leu Gly Asp
1240            1245            1250 gac cct tca cag ccc cag acg aca att tca aag gat cag ttt gaa    4622
Asp Pro Ser Gln Pro Gln Thr Thr Ile Ser Lys Asp Gln Phe Glu
1255            1260            1265 aag aag aaa aat gat acc tta gac ccc gaa cct ttc gtt gat tgc    4667
Lys Lys Lys Asn Asp Thr Leu Asp Pro Glu Pro Phe Val Asp Cys
1270            1275            1280 aag gag tgt ggc cgg aag atg cat cag att tgc gtt ctg cac tat    4712
Lys Glu Cys Gly Arg Lys Met His Gln Ile Cys Val Leu His Tyr
1285            1290            1295 gac atc att tgg cct tca ggt ttt gtg tgc gac aac tgc ttg aag    4757
Asp Ile Ile Trp Pro Ser Gly Phe Val Cys Asp Asn Cys Leu Lys
1300            1305            1310 aaa act ggc aga cct cga aaa gaa aac aaa ttc agt gct aag agg    4802
Lys Thr Gly Arg Pro Arg Lys Glu Asn Lys Phe Ser Ala Lys Arg
1315            1320            1325 ctg cag acc aca aga ctg gga aac cac ttg gaa gac cga gtg aac    4847
Leu Gln Thr Thr Arg Leu Gly Asn His Leu Glu Asp Arg Val Asn
1330            1335            1340 aaa ttt ttg cgg cgc cag aat cac cct gaa gcc ggg gag gtt ttt    4892
Lys Phe Leu Arg Arg Gln Asn His Pro Glu Ala Gly Glu Val Phe
1345            1350            1355 gtc cga gtg gtg gcc agc tca gac aag acg gtg gag gtc aag ccc    4937
Val Arg Val Val Ala Ser Ser Asp Lys Thr Val Glu Val Lys Pro
1360            1365            1370 ggg atg aag tca cgg ttt gtg gat tct ggg gaa atg tct gaa tct    4982
Gly Met Lys Ser Arg Phe Val Asp Ser Gly Glu Met Ser Glu Ser
1375            1380            1385 ttc cca tat cga acc aaa gct ctg ttt gct ttt gag gaa att gac    5027

```
                Phe Pro Tyr Arg Thr Lys Ala Leu Phe Ala Phe Glu Glu Ile Asp
                    1390            1395                1400 ggc gtg gat gtc tgc ttt ttt gga atg cac gtc caa gaa tac ggc              5072
Gly Val Asp Val Cys Phe Phe Gly Met His Val Gln Glu Tyr Gly
1405            1410                1415 tct gat tgc ccc cct cca aac acg agg cgt gtg tac att tct tat              5117
Ser Asp Cys Pro Pro Pro Asn Thr Arg Arg Val Tyr Ile Ser Tyr
1420            1425                1430 ctg gat agt att cat ttc ttc cgg cca cgt tgc ctc cgc aca gcc              5162
Leu Asp Ser Ile His Phe Phe Arg Pro Arg Cys Leu Arg Thr Ala
1435            1440                1445 gtt tac cat gag atc ctt att gga tat tta gag tat gtg aag aaa              5207
Val Tyr His Glu Ile Leu Ile Gly Tyr Leu Glu Tyr Val Lys Lys
1450            1455                1460 tta ggg tat gtg aca ggg cac atc tgg gcc tgt cct cca agt gaa              5252
Leu Gly Tyr Val Thr Gly His Ile Trp Ala Cys Pro Pro Ser Glu
1465            1470                1475 gga gat gat tac atc ttc cat tgc cac cca cct gat caa aaa ata              5297
Gly Asp Asp Tyr Ile Phe His Cys His Pro Pro Asp Gln Lys Ile
1480            1485                1490 ccc aag cca aaa cga ctg cag gag tgg tac aaa aag atg ctg gac              5342
Pro Lys Pro Lys Arg Leu Gln Glu Trp Tyr Lys Lys Met Leu Asp
1495            1500                1505 aag gcg ttt gca gag cgg atc atc cat gac tac aag gat att ttc              5387
Lys Ala Phe Ala Glu Arg Ile Ile His Asp Tyr Lys Asp Ile Phe
1510            1515                1520 aaa caa gca act gaa gac agg ctc acc agt gcc aag gaa ctg ccc              5432
Lys Gln Ala Thr Glu Asp Arg Leu Thr Ser Ala Lys Glu Leu Pro
1525            1530                1535 tat ttt gaa ggt gat ttc tgg ccc aat gtg tta gaa gag agc att              5477
Tyr Phe Glu Gly Asp Phe Trp Pro Asn Val Leu Glu Glu Ser Ile
1540            1545                1550 aag gaa cta gaa caa gaa gaa gag gag agg aaa aag gaa gag agc              5522
Lys Glu Leu Glu Gln Glu Glu Glu Glu Arg Lys Lys Glu Glu Ser
1555            1560                1565 act gca gcc agt gaa acc act gag ggc agt cag ggc gac agc aag              5567
Thr Ala Ala Ser Glu Thr Thr Glu Gly Ser Gln Gly Asp Ser Lys
1570            1575                1580 aat gcc aag aag aag aac aac aag aaa acc aac aag aac aaa agc              5612
Asn Ala Lys Lys Lys Asn Asn Lys Lys Thr Asn Lys Asn Lys Ser
1585            1590                1595 agc atc agc cgc gcc aac aag aag aag ccc agc atg ccc aac gtg              5657
Ser Ile Ser Arg Ala Asn Lys Lys Lys Pro Ser Met Pro Asn Val
1600            1605                1610 tcc aat gac ctg tcc cag aag ctg tat gcc acc atg gag aag cac              5702
Ser Asn Asp Leu Ser Gln Lys Leu Tyr Ala Thr Met Glu Lys His
1615            1620                1625 aag gag gtc ttc ttc gtg atc cac ctg cac gct ggg cct gtc atc              5747
Lys Glu Val Phe Phe Val Ile His Leu His Ala Gly Pro Val Ile
1630            1635                1640 aac acc ctg ccc ccc atc gtc gac ccc gac ccc ctg ctc agc tgt              5792
Asn Thr Leu Pro Pro Ile Val Asp Pro Asp Pro Leu Leu Ser Cys
1645            1650                1655 gac ctc atg gat ggg cgc gac gcc ttc ctc acc ctc gcc aga gac              5837
Asp Leu Met Asp Gly Arg Asp Ala Phe Leu Thr Leu Ala Arg Asp
1660            1665                1670 aag cac tgg gag ttc tcc tcc ttg cgc cgc tcc aag tgg tcc acg              5882
Lys His Trp Glu Phe Ser Ser Leu Arg Arg Ser Lys Trp Ser Thr
1675            1680                1685
```

```
ctc tgc atg ctg gtg gag ctg cac acc cag ggc cag gac cgc ttt    5927
Leu Cys Met Leu Val Glu Leu His Thr Gln Gly Gln Asp Arg Phe
    1690                1695                1700 gtc tac acc tgc aac gag tgc aag cac cac gtg gag acg cgc tgg    5972
Val Tyr Thr Cys Asn Glu Cys Lys His His Val Glu Thr Arg Trp
    1705                1710                1715 cac tgc act gtg tgc gag gac tac gac ctc tgc atc aac tgc tat    6017
His Cys Thr Val Cys Glu Asp Tyr Asp Leu Cys Ile Asn Cys Tyr
    1720                1725                1730 aac acg aag agc cat gcc cat aag atg gtg aag tgg ggg ctg ggc    6062
Asn Thr Lys Ser His Ala His Lys Met Val Lys Trp Gly Leu Gly
    1735                1740                1745 ctg gat gac gag ggc agc agc cag ggc gag cca cag tca aag agc    6107
Leu Asp Asp Glu Gly Ser Ser Gln Gly Glu Pro Gln Ser Lys Ser
    1750                1755                1760 ccc cag gag tca cgc cgg ctg agc atc cag cgc tgc atc cag tcg    6152
Pro Gln Glu Ser Arg Arg Leu Ser Ile Gln Arg Cys Ile Gln Ser
    1765                1770                1775 ctg gtg cac gcg tgc cag tgc cgc aac gcc aac tgc tcg ctg cca    6197
Leu Val His Ala Cys Gln Cys Arg Asn Ala Asn Cys Ser Leu Pro
    1780                1785                1790 tcc tgc cag aag atg aag cgg gtg gtg cag cac acc aag ggc tgc    6242
Ser Cys Gln Lys Met Lys Arg Val Val Gln His Thr Lys Gly Cys
    1795                1800                1805 aaa cgc aag acc aac ggg ggc tgc ccg gtg tgc aag cag ctc atc    6287
Lys Arg Lys Thr Asn Gly Gly Cys Pro Val Cys Lys Gln Leu Ile
    1810                1815                1820 gcc ctc tgc tgc tac cac gcc aag cac tgc caa gaa aac aaa tgc    6332
Ala Leu Cys Cys Tyr His Ala Lys His Cys Gln Glu Asn Lys Cys
    1825                1830                1835 ccc gtg ccc ttc tgc ctc aac atc aaa cac aag ctc cgc cag cag    6377
Pro Val Pro Phe Cys Leu Asn Ile Lys His Lys Leu Arg Gln Gln
    1840                1845                1850 cag atc cag cac cgc ctg cag cag gcc cag ctc atg cgc cgg cgg    6422
Gln Ile Gln His Arg Leu Gln Gln Ala Gln Leu Met Arg Arg Arg
    1855                1860                1865 atg gcc acc atg aac acc cgc aac gtg cct cag cag agt ctg cct    6467
Met Ala Thr Met Asn Thr Arg Asn Val Pro Gln Gln Ser Leu Pro
    1870                1875                1880 tct cct acc tca gca ccg ccc ggg acc ccc aca cag cag ccc agc    6512
Ser Pro Thr Ser Ala Pro Pro Gly Thr Pro Thr Gln Gln Pro Ser
    1885                1890                1895 aca ccc cag acg ccg cag ccc cct gcc cag ccc caa ccc tca ccc    6557
Thr Pro Gln Thr Pro Gln Pro Pro Ala Gln Pro Gln Pro Ser Pro
    1900                1905                1910 gtg agc atg tca cca gct ggc ttc ccc agc gtg gcc cgg act cag    6602
Val Ser Met Ser Pro Ala Gly Phe Pro Ser Val Ala Arg Thr Gln
    1915                1920                1925 ccc ccc acc acg gtg tcc aca ggg aag cct acc agc cag gtg ccg    6647
Pro Pro Thr Thr Val Ser Thr Gly Lys Pro Thr Ser Gln Val Pro
    1930                1935                1940 gcc ccc cca ccc ccg gcc cag ccc cct cct gca gcg gtg gaa gcg    6692
Ala Pro Pro Pro Pro Ala Gln Pro Pro Pro Ala Ala Val Glu Ala
    1945                1950                1955 gct cgg cag atc gag cgt gag gcc cag cag cag cag cac ctg tac    6737
Ala Arg Gln Ile Glu Arg Glu Ala Gln Gln Gln Gln His Leu Tyr
    1960                1965                1970 cgg gtg aac atc aac aac agc atg ccc cca gga cgc acg ggc atg    6782
Arg Val Asn Ile Asn Asn Ser Met Pro Pro Gly Arg Thr Gly Met
    1975                1980                1985
```

-continued

```
ggg  acc  ccg  ggg  agc  cag  atg  gcc  ccc  gtg  agc  ctg  aat  gtg  ccc        6827
Gly  Thr  Pro  Gly  Ser  Gln  Met  Ala  Pro  Val  Ser  Leu  Asn  Val  Pro
     1990                1995                     2000 cga  ccc  aac  cag  gtg  agc  ggg  ccc  gtc  atg  ccc  agc  atg  cct  ccc        6872
Arg  Pro  Asn  Gln  Val  Ser  Gly  Pro  Val  Met  Pro  Ser  Met  Pro  Pro
     2005                2010                     2015 ggg  cag  tgg  cag  cag  gcg  ccc  ctt  ccc  cag  cag  ccc  atg  cca             6917
Gly  Gln  Trp  Gln  Gln  Ala  Pro  Leu  Pro  Gln  Gln  Pro  Met  Pro
     2020                2025                     2030 ggc  ttg  ccc  agg  cct  gtg  ata  tcc  atg  cag  gcc  cag  gcg  gcc  gtg        6962
Gly  Leu  Pro  Arg  Pro  Val  Ile  Ser  Met  Gln  Ala  Gln  Ala  Ala  Val
     2035                2040                     2045 gct  ggg  ccc  cgg  atg  ccc  agc  gtg  cag  cca  ccc  agg  agc  atc  tca        7007
Ala  Gly  Pro  Arg  Met  Pro  Ser  Val  Gln  Pro  Pro  Arg  Ser  Ile  Ser
     2050                2055                     2060 ccc  agc  gct  ctg  caa  gac  ctg  ctg  cgg  acc  ctg  aag  tcg  ccc  agc        7052
Pro  Ser  Ala  Leu  Gln  Asp  Leu  Leu  Arg  Thr  Leu  Lys  Ser  Pro  Ser
     2065                2070                     2075 tcc  cct  cag  cag  caa  cag  cag  gtg  ctg  aac  att  ctc  aaa  tca  aac        7097
Ser  Pro  Gln  Gln  Gln  Gln  Gln  Val  Leu  Asn  Ile  Leu  Lys  Ser  Asn
     2080                2085                     2090 ccg  cag  cta  atg  gca  gct  ttc  atc  aaa  cag  cgc  aca  gcc  aag  tac        7142
Pro  Gln  Leu  Met  Ala  Ala  Phe  Ile  Lys  Gln  Arg  Thr  Ala  Lys  Tyr
     2095                2100                     2105 gtg  gcc  aat  cag  ccc  ggc  atg  cag  ccc  cag  cct  ggc  ctc  cag  tcc        7187
Val  Ala  Asn  Gln  Pro  Gly  Met  Gln  Pro  Gln  Pro  Gly  Leu  Gln  Ser
     2110                2115                     2120 cag  ccc  ggc  atg  caa  ccc  cag  cct  ggc  atg  cac  cag  cag  ccc  agc        7232
Gln  Pro  Gly  Met  Gln  Pro  Gln  Pro  Gly  Met  His  Gln  Gln  Pro  Ser
     2125                2130                     2135 ctg  cag  aac  ctg  aat  gcc  atg  cag  gct  ggc  gtg  ccg  cgg  ccc  ggt        7277
Leu  Gln  Asn  Leu  Asn  Ala  Met  Gln  Ala  Gly  Val  Pro  Arg  Pro  Gly
     2140                2145                     2150 gtg  cct  cca  cag  cag  cag  gcg  atg  gga  ggc  ctg  aac  ccc  cag  ggc        7322
Val  Pro  Pro  Gln  Gln  Gln  Ala  Met  Gly  Gly  Leu  Asn  Pro  Gln  Gly
     2155                2160                     2165 cag  gcc  ttg  aac  atc  atg  aac  cca  gga  cac  aac  ccc  aac  atg  gcg        7367
Gln  Ala  Leu  Asn  Ile  Met  Asn  Pro  Gly  His  Asn  Pro  Asn  Met  Ala
     2170                2175                     2180 agt  atg  aat  cca  cag  tac  cga  gaa  atg  tta  cgg  agg  cag  ctg  ctg        7412
Ser  Met  Asn  Pro  Gln  Tyr  Arg  Glu  Met  Leu  Arg  Arg  Gln  Leu  Leu
     2185                2190                     2195 cag  cag  cag  cag  caa  cag  cag  caa  caa  cag  cag  caa  cag  cag             7457
Gln  Gln  Gln  Gln  Gln  Gln  Gln  Gln  Gln  Gln  Gln  Gln  Gln  Gln
     2200                2205                     2210 cag  cag  caa  ggg  agt  gcc  ggc  atg  gct  ggg  ggc  atg  gcg  ggg  cac        7502
Gln  Gln  Gln  Gly  Ser  Ala  Gly  Met  Ala  Gly  Gly  Met  Ala  Gly  His
     2215                2220                     2225 ggc  cag  ttc  cag  cag  cct  caa  gga  ccc  gga  ggc  tac  cca  ccg  gcc        7547
Gly  Gln  Phe  Gln  Gln  Pro  Gln  Gly  Pro  Gly  Gly  Tyr  Pro  Pro  Ala
     2230                2235                     2240 atg  cag  cag  cag  cag  cgc  atg  cag  cag  cat  ctc  ccc  ctc  cag  ggc        7592
Met  Gln  Gln  Gln  Gln  Arg  Met  Gln  Gln  His  Leu  Pro  Leu  Gln  Gly
     2245                2250                     2255 agc  tcc  atg  ggc  cag  atg  gcg  gct  cag  atg  gga  cag  ctt  ggc  cag        7637
Ser  Ser  Met  Gly  Gln  Met  Ala  Ala  Gln  Met  Gly  Gln  Leu  Gly  Gln
     2260                2265                     2270 atg  ggg  cag  ccg  ggg  ctg  ggg  gca  gac  agc  acc  ccc  aac  atc  cag        7682
Met  Gly  Gln  Pro  Gly  Leu  Gly  Ala  Asp  Ser  Thr  Pro  Asn  Ile  Gln
```

```
                  2275                2280                2285
caa gcc ctg cag cag cgg att ctg cag caa cag cag atg aag cag        7727
Gln Ala Leu Gln Gln Arg Ile Leu Gln Gln Gln Gln Met Lys Gln
    2290                2295                2300 cag att ggg tcc cca ggc cag ccg aac ccc atg agc ccc cag caa        7772
Gln Ile Gly Ser Pro Gly Gln Pro Asn Pro Met Ser Pro Gln Gln
2305                2310                2315 cac atg ctc tca gga cag cca cag gcc tcg cat ctc cct ggc cag        7817
His Met Leu Ser Gly Gln Pro Gln Ala Ser His Leu Pro Gly Gln
    2320                2325                2330 cag atc gcc acg tcc ctt agt aac cag gtg cgg tct cca gcc cct        7862
Gln Ile Ala Thr Ser Leu Ser Asn Gln Val Arg Ser Pro Ala Pro
    2335                2340                2345 gtc cag tct cca cgg ccc cag tcc cag cct cca cat tcc agc ccg        7907
Val Gln Ser Pro Arg Pro Gln Ser Gln Pro Pro His Ser Ser Pro
2350                2355                2360 tca cca cgg ata cag ccc cag cct tcg cca cac cac gtc tca ccc        7952
Ser Pro Arg Ile Gln Pro Gln Pro Ser Pro His His Val Ser Pro
    2365                2370                2375 cag act ggt tcc ccc cac ccc gga ctc gca gtc acc atg gcc agc        7997
Gln Thr Gly Ser Pro His Pro Gly Leu Ala Val Thr Met Ala Ser
    2380                2385                2390 tcc ata gat cag gga cac ttg ggg aac ccc gaa cag agt gca atg        8042
Ser Ile Asp Gln Gly His Leu Gly Asn Pro Glu Gln Ser Ala Met
    2395                2400                2405 ctc ccc cag ctg aac acc ccc agc agg agt gcg ctg tcc agc gaa        8087
Leu Pro Gln Leu Asn Thr Pro Ser Arg Ser Ala Leu Ser Ser Glu
    2410                2415                2420 ctg tcc ctg gtc ggg gac acc acg ggg gac acg cta gag aag ttt        8132
Leu Ser Leu Val Gly Asp Thr Thr Gly Asp Thr Leu Glu Lys Phe
2425                2430                2435 gtg gag ggc ttg tag                                                8147
Val Glu Gly Leu
    2440

<210> SEQ ID NO 10
<211> LENGTH: 2442
<212> TYPE: PRT
<213> ORGANISM: human

<400> SEQUENCE: 10

Met Ala Glu Asn Leu Leu Asp Gly Pro Pro Asn Pro Lys Arg Ala Lys
1               5                   10                  15

Leu Ser Ser Pro Gly Phe Ser Ala Asn Asp Ser Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
        115                 120                 125

Ser Ala Pro Ser Leu Pro Lys Gln Ala Ala Ser Thr Ser Gly Pro Thr
```

```
            130                 135                 140
Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
        195                 200                 205

Met Asn Gly Ser Leu Gly Ala Ala Gly Arg Gly Arg Gly Ala Gly Met
    210                 215                 220

Pro Tyr Pro Thr Pro Ala Met Gln Gly Ala Ser Ser Val Leu Ala
225                 230                 235                 240

Glu Thr Leu Thr Gln Val Ser Pro Gln Met Thr Gly His Ala Gly Leu
                245                 250                 255

Asn Thr Ala Gln Ala Gly Gly Met Ala Lys Met Gly Ile Thr Gly Asn
            260                 265                 270

Thr Ser Pro Phe Gly Gln Pro Phe Ser Gln Ala Gly Gly Gln Pro Met
        275                 280                 285

Gly Ala Thr Gly Val Asn Pro Gln Leu Ala Ser Lys Gln Ser Met Val
    290                 295                 300

Asn Ser Leu Pro Thr Phe Pro Thr Asp Ile Lys Asn Thr Ser Val Thr
305                 310                 315                 320

Asn Val Pro Asn Met Ser Gln Met Gln Thr Ser Val Gly Ile Val Pro
                325                 330                 335

Thr Gln Ala Ile Ala Thr Gly Pro Thr Ala Asp Pro Glu Lys Arg Lys
            340                 345                 350

Leu Ile Gln Gln Gln Leu Val Leu Leu Leu His Ala His Lys Cys Gln
        355                 360                 365

Arg Arg Glu Gln Ala Asn Gly Glu Val Arg Ala Cys Ser Leu Pro His
    370                 375                 380

Cys Arg Thr Met Lys Asn Val Leu Asn His Met Thr His Cys Gln Ala
385                 390                 395                 400

Gly Lys Ala Cys Gln Val Ala His Cys Ala Ser Ser Arg Gln Ile Ile
                405                 410                 415

Ser His Trp Lys Asn Cys Thr Arg His Asp Cys Pro Val Cys Leu Pro
            420                 425                 430

Leu Lys Asn Ala Ser Asp Lys Arg Asn Gln Gln Thr Ile Leu Gly Ser
        435                 440                 445

Pro Ala Ser Gly Ile Gln Asn Thr Ile Gly Ser Val Gly Thr Gly Gln
    450                 455                 460

Gln Asn Ala Thr Ser Leu Ser Asn Pro Asn Pro Ile Asp Pro Ser Ser
465                 470                 475                 480

Met Gln Arg Ala Tyr Ala Ala Leu Gly Leu Pro Tyr Met Asn Gln Pro
                485                 490                 495

Gln Thr Gln Leu Gln Pro Gln Val Pro Gly Gln Gln Pro Ala Gln Pro
            500                 505                 510

Gln Thr His Gln Gln Met Arg Thr Leu Asn Pro Leu Gly Asn Asn Pro
        515                 520                 525

Met Asn Ile Pro Ala Gly Gly Ile Thr Thr Asp Gln Gln Pro Pro Asn
    530                 535                 540

Leu Ile Ser Glu Ser Ala Leu Pro Thr Ser Leu Gly Ala Thr Asn Pro
545                 550                 555                 560
```

```
Leu Met Asn Asp Gly Ser Asn Ser Gly Asn Ile Gly Thr Leu Ser Thr
            565                 570                 575

Ile Pro Thr Ala Ala Pro Pro Ser Ser Thr Gly Val Arg Lys Gly Trp
            580                 585                 590

His Glu His Val Thr Gln Asp Leu Arg Ser His Leu Val His Lys Leu
            595                 600                 605

Val Gln Ala Ile Phe Pro Thr Pro Asp Pro Ala Ala Leu Lys Asp Arg
            610                 615                 620

Arg Met Glu Asn Leu Val Ala Tyr Ala Lys Lys Val Glu Gly Asp Met
625                 630                 635                 640

Tyr Glu Ser Ala Asn Ser Arg Asp Glu Tyr Tyr His Leu Leu Ala Glu
            645                 650                 655

Lys Ile Tyr Lys Ile Gln Lys Glu Leu Glu Glu Lys Arg Arg Ser Arg
            660                 665                 670

Leu His Lys Gln Gly Ile Leu Gly Asn Gln Pro Ala Leu Pro Ala Pro
            675                 680                 685

Gly Ala Gln Pro Pro Val Ile Pro Gln Ala Gln Pro Val Arg Pro Pro
            690                 695                 700

Asn Gly Pro Leu Ser Leu Pro Val Asn Arg Met Gln Val Ser Gln Gly
705                 710                 715                 720

Met Asn Ser Phe Asn Pro Met Ser Leu Gly Asn Val Gln Leu Pro Gln
            725                 730                 735

Ala Pro Met Gly Pro Arg Ala Ala Ser Pro Met Asn His Ser Val Gln
            740                 745                 750

Met Asn Ser Met Gly Ser Val Pro Gly Met Ala Ile Ser Pro Ser Arg
            755                 760                 765

Met Pro Gln Pro Pro Asn Met Met Gly Ala His Thr Asn Asn Met Met
            770                 775                 780

Ala Gln Ala Pro Ala Gln Ser Gln Phe Leu Pro Gln Asn Gln Phe Pro
785                 790                 795                 800

Ser Ser Ser Gly Ala Met Ser Val Gly Met Gly Gln Pro Pro Ala Gln
            805                 810                 815

Thr Gly Val Ser Gln Gly Gln Val Pro Gly Ala Ala Leu Pro Asn Pro
            820                 825                 830

Leu Asn Met Leu Gly Pro Gln Ala Ser Gln Leu Pro Cys Pro Pro Val
            835                 840                 845

Thr Gln Ser Pro Leu His Pro Thr Pro Pro Ala Ser Thr Ala Ala
            850                 855                 860

Gly Met Pro Ser Leu Gln His Thr Thr Pro Pro Gly Met Thr Pro Pro
865                 870                 875                 880

Gln Pro Ala Ala Pro Thr Gln Pro Ser Thr Pro Val Ser Ser Ser Gly
            885                 890                 895

Gln Thr Pro Thr Pro Thr Pro Gly Ser Val Pro Ser Ala Thr Gln Thr
            900                 905                 910

Gln Ser Thr Pro Thr Val Gln Ala Ala Ala Gln Ala Gln Val Thr Pro
            915                 920                 925

Gln Pro Gln Thr Pro Val Gln Pro Pro Ser Val Ala Thr Pro Gln Ser
            930                 935                 940

Ser Gln Gln Gln Pro Thr Pro Val His Ala Gln Pro Pro Gly Thr Pro
945                 950                 955                 960

Leu Ser Gln Ala Ala Ala Ser Ile Asp Asn Arg Val Pro Thr Pro Ser
            965                 970                 975
```

```
Ser Val Ala Ser Ala Glu Thr Asn Ser Gln Gln Pro Gly Pro Asp Val
            980                 985                 990

Pro Val Leu Glu Met Lys Thr Glu  Thr Gln Ala Glu Asp  Thr Glu Pro
            995                 1000                1005

Asp Pro Gly Glu Ser Lys Gly  Glu Pro Arg Ser Glu  Met Met Glu
    1010                1015                1020

Glu Asp Leu Gln Gly Ala Ser  Gln Val Lys Glu Glu  Thr Asp Ile
    1025                1030                1035

Ala Glu Gln Lys Ser Glu Pro  Met Glu Val Asp Glu  Lys Lys Pro
    1040                1045                1050

Glu Val Lys Val Glu Val Lys  Glu Glu Glu Glu Ser  Ser Ser Asn
    1055                1060                1065

Gly Thr Ala Ser Gln Ser Thr  Ser Pro Ser Gln Pro  Arg Lys Lys
    1070                1075                1080

Ile Phe Lys Pro Glu Glu Leu  Arg Gln Ala Leu Met  Pro Thr Leu
    1085                1090                1095

Glu Ala Leu Tyr Arg Gln Asp  Pro Glu Ser Leu Pro  Phe Arg Gln
    1100                1105                1110

Pro Val Asp Pro Gln Leu Leu  Gly Ile Pro Asp Tyr  Phe Asp Ile
    1115                1120                1125

Val Lys Asn Pro Met Asp Leu  Ser Thr Ile Lys Arg  Lys Leu Asp
    1130                1135                1140

Thr Gly Gln Tyr Gln Glu Pro  Trp Gln Tyr Val Asp  Asp Val Trp
    1145                1150                1155

Leu Met Phe Asn Asn Ala Trp  Leu Tyr Asn Arg Lys  Thr Ser Arg
    1160                1165                1170

Val Tyr Lys Phe Cys Ser Lys  Leu Ala Glu Val Phe  Glu Gln Glu
    1175                1180                1185

Ile Asp Pro Val Met Gln Ser  Leu Gly Tyr Cys Cys  Gly Arg Lys
    1190                1195                1200

Tyr Glu Phe Ser Pro Gln Thr  Leu Cys Cys Tyr Gly  Lys Gln Leu
    1205                1210                1215

Cys Thr Ile Pro Arg Asp Ala  Ala Tyr Tyr Ser Tyr  Gln Asn Arg
    1220                1225                1230

Tyr His Phe Cys Glu Lys Cys  Phe Thr Glu Ile Gln  Gly Glu Asn
    1235                1240                1245

Val Thr Leu Gly Asp Asp Pro  Ser Gln Pro Gln Thr  Thr Ile Ser
    1250                1255                1260

Lys Asp Gln Phe Glu Lys Lys  Lys Asn Asp Thr Leu  Asp Pro Glu
    1265                1270                1275

Pro Phe Val Asp Cys Lys Glu  Cys Gly Arg Lys Met  His Gln Ile
    1280                1285                1290

Cys Val Leu His Tyr Asp Ile  Ile Trp Pro Ser Gly  Phe Val Cys
    1295                1300                1305

Asp Asn Cys Leu Lys Lys Thr  Gly Arg Pro Arg Lys  Glu Asn Lys
    1310                1315                1320

Phe Ser Ala Lys Arg Leu Gln  Thr Thr Arg Leu Gly  Asn His Leu
    1325                1330                1335

Glu Asp Arg Val Asn Lys Phe  Leu Arg Arg Gln Asn  His Pro Glu
    1340                1345                1350

Ala Gly Glu Val Phe Val Arg  Val Val Ala Ser Ser  Asp Lys Thr
    1355                1360                1365

Val Glu Val Lys Pro Gly Met  Lys Ser Arg Phe Val  Asp Ser Gly
```

-continued

```
              1370                1375                1380
Glu  Met  Ser  Glu  Ser  Phe  Pro  Tyr  Arg  Thr  Lys  Ala  Leu  Phe  Ala
     1385                1390                1395
Phe  Glu  Glu  Ile  Asp  Gly  Val  Asp  Val  Cys  Phe  Phe  Gly  Met  His
     1400                1405                1410
Val  Gln  Glu  Tyr  Gly  Ser  Asp  Cys  Pro  Pro  Asn  Thr  Arg  Arg
     1415                1420                1425
Val  Tyr  Ile  Ser  Tyr  Leu  Asp  Ser  Ile  His  Phe  Arg  Pro  Arg
     1430                1435                1440
Cys  Leu  Arg  Thr  Ala  Val  Tyr  His  Glu  Ile  Leu  Ile  Gly  Tyr  Leu
     1445                1450                1455
Glu  Tyr  Val  Lys  Lys  Leu  Gly  Tyr  Val  Thr  Gly  His  Ile  Trp  Ala
     1460                1465                1470
Cys  Pro  Pro  Ser  Glu  Gly  Asp  Asp  Tyr  Ile  Phe  His  Cys  His  Pro
     1475                1480                1485
Pro  Asp  Gln  Lys  Ile  Pro  Lys  Pro  Lys  Arg  Leu  Gln  Glu  Trp  Tyr
     1490                1495                1500
Lys  Lys  Met  Leu  Asp  Lys  Ala  Phe  Ala  Glu  Arg  Ile  Ile  His  Asp
     1505                1510                1515
Tyr  Lys  Asp  Ile  Phe  Lys  Gln  Ala  Thr  Glu  Asp  Arg  Leu  Thr  Ser
     1520                1525                1530
Ala  Lys  Glu  Leu  Pro  Tyr  Phe  Glu  Gly  Asp  Phe  Trp  Pro  Asn  Val
     1535                1540                1545
Leu  Glu  Glu  Ser  Ile  Lys  Glu  Leu  Glu  Gln  Glu  Glu  Glu  Glu  Arg
     1550                1555                1560
Lys  Lys  Glu  Glu  Ser  Thr  Ala  Ala  Ser  Glu  Thr  Thr  Glu  Gly  Ser
     1565                1570                1575
Gln  Gly  Asp  Ser  Lys  Asn  Ala  Lys  Lys  Lys  Asn  Lys  Lys  Thr
     1580                1585                1590
Asn  Lys  Asn  Lys  Ser  Ser  Ile  Ser  Arg  Ala  Asn  Lys  Lys  Lys  Pro
     1595                1600                1605
Ser  Met  Pro  Asn  Val  Ser  Asn  Asp  Leu  Ser  Gln  Lys  Leu  Tyr  Ala
     1610                1615                1620
Thr  Met  Glu  Lys  His  Lys  Glu  Val  Phe  Phe  Val  Ile  His  Leu  His
     1625                1630                1635
Ala  Gly  Pro  Val  Ile  Asn  Thr  Leu  Pro  Pro  Ile  Val  Asp  Pro  Asp
     1640                1645                1650
Pro  Leu  Leu  Ser  Cys  Asp  Leu  Met  Asp  Gly  Arg  Asp  Ala  Phe  Leu
     1655                1660                1665
Thr  Leu  Ala  Arg  Asp  Lys  His  Trp  Glu  Phe  Ser  Ser  Leu  Arg  Arg
     1670                1675                1680
Ser  Lys  Trp  Ser  Thr  Leu  Cys  Met  Leu  Val  Glu  Leu  His  Thr  Gln
     1685                1690                1695
Gly  Gln  Asp  Arg  Phe  Val  Tyr  Thr  Cys  Asn  Glu  Cys  Lys  His  His
     1700                1705                1710
Val  Glu  Thr  Arg  Trp  His  Cys  Thr  Val  Cys  Glu  Asp  Tyr  Asp  Leu
     1715                1720                1725
Cys  Ile  Asn  Cys  Tyr  Asn  Thr  Lys  Ser  His  Ala  His  Lys  Met  Val
     1730                1735                1740
Lys  Trp  Gly  Leu  Gly  Leu  Asp  Asp  Glu  Gly  Ser  Ser  Gln  Gly  Glu
     1745                1750                1755
Pro  Gln  Ser  Lys  Ser  Pro  Gln  Glu  Ser  Arg  Arg  Leu  Ser  Ile  Gln
     1760                1765                1770
```

-continued

```
Arg Cys Ile Gln Ser Leu Val His Ala Cys Gln Cys Arg Asn Ala
1775                1780                1785
Asn Cys Ser Leu Pro Ser Cys Gln Lys Met Lys Arg Val Val Gln
1790                1795                1800
His Thr Lys Gly Cys Lys Arg Lys Thr Asn Gly Gly Cys Pro Val
1805                1810                1815
Cys Lys Gln Leu Ile Ala Leu Cys Cys Tyr His Ala Lys His Cys
1820                1825                1830
Gln Glu Asn Lys Cys Pro Val Pro Phe Cys Leu Asn Ile Lys His
1835                1840                1845
Lys Leu Arg Gln Gln Ile Gln His Arg Leu Gln Gln Ala Gln
1850                1855                1860
Leu Met Arg Arg Arg Met Ala Thr Met Asn Thr Arg Asn Val Pro
1865                1870                1875
Gln Gln Ser Leu Pro Ser Pro Thr Ser Ala Pro Pro Gly Thr Pro
1880                1885                1890
Thr Gln Gln Pro Ser Thr Pro Gln Thr Pro Gln Pro Pro Ala Gln
1895                1900                1905
Pro Gln Pro Ser Pro Val Ser Met Ser Pro Ala Gly Phe Pro Ser
1910                1915                1920
Val Ala Arg Thr Gln Pro Pro Thr Thr Val Ser Thr Gly Lys Pro
1925                1930                1935
Thr Ser Gln Val Pro Ala Pro Pro Pro Pro Ala Gln Pro Pro Pro
1940                1945                1950
Ala Ala Val Glu Ala Ala Arg Gln Ile Glu Arg Glu Ala Gln Gln
1955                1960                1965
Gln Gln His Leu Tyr Arg Val Asn Ile Asn Asn Ser Met Pro Pro
1970                1975                1980
Gly Arg Thr Gly Met Gly Thr Pro Gly Ser Gln Met Ala Pro Val
1985                1990                1995
Ser Leu Asn Val Pro Arg Pro Asn Gln Val Ser Gly Pro Val Met
2000                2005                2010
Pro Ser Met Pro Pro Gly Gln Trp Gln Gln Ala Pro Leu Pro Gln
2015                2020                2025
Gln Gln Pro Met Pro Gly Leu Pro Arg Pro Val Ile Ser Met Gln
2030                2035                2040
Ala Gln Ala Ala Val Ala Gly Pro Arg Met Pro Ser Val Gln Pro
2045                2050                2055
Pro Arg Ser Ile Ser Pro Ser Ala Leu Gln Asp Leu Leu Arg Thr
2060                2065                2070
Leu Lys Ser Pro Ser Ser Pro Gln Gln Gln Gln Val Leu Asn
2075                2080                2085
Ile Leu Lys Ser Asn Pro Gln Leu Met Ala Ala Phe Ile Lys Gln
2090                2095                2100
Arg Thr Ala Lys Tyr Val Ala Asn Gln Pro Gly Met Gln Pro Gln
2105                2110                2115
Pro Gly Leu Gln Ser Gln Pro Gly Met Gln Pro Gln Pro Gly Met
2120                2125                2130
His Gln Gln Pro Ser Leu Gln Asn Leu Asn Ala Met Gln Ala Gly
2135                2140                2145
Val Pro Arg Pro Gly Val Pro Pro Gln Gln Gln Ala Met Gly Gly
2150                2155                2160
```

-continued

```
Leu Asn Pro Gln Gly Gln Ala Leu Asn Ile Met Asn Pro Gly His
    2165            2170            2175

Asn Pro Asn Met Ala Ser Met Asn Pro Gln Tyr Arg Glu Met Leu
    2180            2185            2190

Arg Arg Gln Leu Leu Gln Gln Gln Gln Gln Gln Gln Gln Gln Gln
    2195            2200            2205

Gln Gln Gln Gln Gln Gln Gln Gln Gly Ser Ala Gly Met Ala Gly
    2210            2215            2220

Gly Met Ala Gly His Gly Gln Phe Gln Gln Pro Gln Gly Pro Gly
    2225            2230            2235

Gly Tyr Pro Pro Ala Met Gln Gln Gln Gln Arg Met Gln Gln His
    2240            2245            2250

Leu Pro Leu Gln Gly Ser Ser Met Gly Gln Met Ala Ala Gln Met
    2255            2260            2265

Gly Gln Leu Gly Gln Met Gly Gln Pro Gly Leu Gly Ala Asp Ser
    2270            2275            2280

Thr Pro Asn Ile Gln Gln Ala Leu Gln Gln Arg Ile Leu Gln Gln
    2285            2290            2295

Gln Gln Met Lys Gln Gln Ile Gly Ser Pro Gly Gln Pro Asn Pro
    2300            2305            2310

Met Ser Pro Gln Gln His Met Leu Ser Gly Gln Pro Gln Ala Ser
    2315            2320            2325

His Leu Pro Gly Gln Gln Ile Ala Thr Ser Leu Ser Asn Gln Val
    2330            2335            2340

Arg Ser Pro Ala Pro Val Gln Ser Pro Arg Pro Gln Ser Gln Pro
    2345            2350            2355

Pro His Ser Ser Pro Ser Pro Arg Ile Gln Pro Gln Pro Ser Pro
    2360            2365            2370

His His Val Ser Pro Gln Thr Gly Ser Pro His Pro Gly Leu Ala
    2375            2380            2385

Val Thr Met Ala Ser Ser Ile Asp Gln Gly His Leu Gly Asn Pro
    2390            2395            2400

Glu Gln Ser Ala Met Leu Pro Gln Leu Asn Thr Pro Ser Arg Ser
    2405            2410            2415

Ala Leu Ser Ser Glu Leu Ser Leu Val Gly Asp Thr Thr Gly Asp
    2420            2425            2430

Thr Leu Glu Lys Phe Val Glu Gly Leu
    2435            2440
```

METHOD FOR IDENTIFYING OR SCREENING AGONIST AND ANTAGONIST TO PPAR

This is a continuation-in-part application of PCT application No. PCT/JP98/03734 filed Aug. 24, 1998 claiming a priority of Japanese Patent Application No. 231084/1997 of Aug. 27, 1997, now abandoned.

BACKGROUND OF THE INVENTION

1. Technical Field

This invention relates to a novel method for identifying or screening an agonist for and/or antagonist to peroxisome proliferator activated receptor (PPAR).

2. Background Art

Peroxisome, an organelle found in the cells of animals and plants, contains a group of enzymes participating in the lipometabolism and absorption of lipids such as cholesterol. An increase in peroxisome is also induced by diet or physiological factors. It is known that a group of chemicals diversified in structure including antilipemic (fibrates), insecticides and plasticizers such as phthalic acids when they are administered dramatically increase the size and number of peroxisome in liver and kidney and at the same time elevate the ability of metabolizing fatty acids in peroxisome through intermediary of an increase in the expression of enzymes necessary for the β-oxidation cycle. Hence, they are called peroxisome proliferator. Among studies on the mechanism of such a peroxisome proliferation, a nuclear receptor that is activated by the group of chemicals has been identified and named peroxisome proliferator activated receptor (PPAR).

From its structure, etc., PPAR is considered to be a member of nuclear receptor (nuclear hormone receptor) super family. Like other nuclear receptors, it is activated by its binding to a ligand, and its binding to a response sequence (PPRE: peroxisome proliferator response element) existing upstream of a target gene domain activates transcription of the target gene. PPAR is known to form a heterodimer with a retinoid X receptor (RXR) and binds to PPRE in the form of the heterodimer. Also, like other nuclear receptors, PPAR is considered to have the interaction with a group of transcription coactivators (coactivators) in order to exhibit its transcription activation activity.

Hitherto, three kinds of PPAR subtypes called PPARα, PPARδ (or NUC-1, PEARβ, FAAR) and PPARγ have been identified and their genes (cDNA) have been cloned (Lemberger et al., Annu. Rev. Cell. Dev. Biol., vol. 12, pp. 335–363, 1996). Of the three kinds, PPARγ is expressed particularly in an adipose tissue and considered to be a factor that closely participates in differentiation of adipocytes (Tontonoz et al., Genes and Development, vol. 8, pp. 1224–1234, 1994; Tontonoz et al., Cell, vol. 79, pp. 1147–1156, 1994).

On the other hand, various thiazolidinedione derivatives show hypoglycemic effect in a model animal of non-insulin-dependent diabetes mellitus (NIDDM) and are expected as a NIDDM remedy having an insulin resistance releasing effect. These thiazolidinedione derivatives act as ligands to PPARγ and specifically activate PPARγ, which has been discovered in recent studies (Lehmann et al., Journal of Biological Chemistry, vol. 270, pp. 12953–12956, 1995). Since a strong correlation is observed between such a PPARγ activation ability of thiazolidinedione derivatives and the hypoglycemic effect in a hereditary obese mouse, PPARγ is considered to be a target molecule of the pharmaceutical effect of the thiazolidinedione derivatives (Willson et al., Journal of Medicinal Chemistry, vol. 39, pp. 665–668, 1996). This also relates to the fact that an adipose tissue where PPARγ is specifically expressed is an organ that plays an important role in maintaining energy balance. From these findings, a compound specifically acting as an agonist for PPARγ is considered to be very useful as a remedy for diabetes mellitus.

However, to date, those methods known as screening methods for PPAR acting agents each involve the problems that operation is complicated and simultaneous treatment of multiple samples is difficult.

For example, there has been known a method for examining PPAR activation ability of a sample using animal cells having introduced therein reporter plasmid containing a reporter gene linked to a PPAR expression vector and a PPAR response element (PPRE), with using as an index a change in the amount of expression of a reporter gene in the cells (WO 96/22884, Tontonoz et al., Genes and Development, vol. 8, pp. 1224–1234, 1994). As its improved method, there has been known a method using animal cells having introduced therein vector for expressing fused protein in which the DNA binding domain of GAL4, i.e., the transcription factor of yeast, and the ligand binding domain of PPAR linked together, along with having introduced a reporter plasmid containing a reporter gene linked to the response element of GAL4 (GAL4 binding element) (WO 96/33724, Lehmann et al., Journal of Biological Chemistry, vol. 270, pp. 12953–12956, 1995; Willson et al., Journal of Medicinal Chemistry, vol. 39, pp. 665–668, 1996). In these methods, an extrinsic gene is introduced into animal cells. Upon the introduction of gene, it is sometimes the case that the integration of a gene into a chromosome has taken place, the gene is influenced by the site where the gene is integrated. Therefore, it is necessary to use a transformed cell in which gene is not influenced by the chromosome. To acquire such a transformed animal cell and express an extrinsic gene stably are accompanied by technical difficulties. Since coactivators, RXR, etc. derived from host animal are considered to participate in the activation of transcription in these methods, there is the possibility that the action of the test substance to PPAR alone cannot be detected surely.

As a method for directly detecting the binding between PPAR and a ligand without using any animal cell or reporter gene, there has been known a method for examining binding and antagonism between a fused protein comprising the ligand binding domain of PPAR and glutathione-S-transferase (GST) and a test compound labeled with a radioisotope (Willson et al., Journal of Medicinal Chemistry, vol. 39, pp. 665–668, 1996; Buckle et al., Bioorganic & Medical Chemistry Letters, vol. 6, pp. 2121–2126, 1996). Recently, it has been elucidated that like other nuclear receptor RXR, etc., PPAR interacts with SRC-1, one of coactivators, ligand-dependently. Based on this finding, Krey et al. reported a method for detecting the action of a test compound as a ligand using a fused protein comprising the ligand binding domain of PPAR and glutathione-S-transferase (GST) and SRC-1 labeled with a radioisotope (Krey et al., Molecular Endocrinology, Vol. 11, pp. 779–791, 1997). However, these methods each use a label of radioisotope and therefore it is accompanied by a danger and has a limitation in treating power since preparation of a labeled compound or coactivator on a large scale is difficult.

As described above, upon screening PPAR acting agents, a screening method which is simple, high precision, and efficient has been desired.

An object of this invention is to provide a novel method for identifying and screening an agonist and/or antagonist to peroxisome proliferator activated receptor (PPAR).

The present inventors have uniquely found that in addition to SRC-1, one of the coactivators, that is already known to interact with PPAR, CBP (CREB-binding protein) interacts with PPAR ligand-dependently and identified the binding domain of the coactivator to PPAR. Further, based on these findings, they have completed a method for identifying or screening a novel PPAR acting agent that detects a ligand-dependent interaction between PPAR and a coactivator using a Two-hybrid system of yeast.

SUMMARY OF THE INVENTION

This invention relates to a method for identifying or screening an agonist for or antagonist to a peroxisome proliferator-activated receptor (PPAR), which comprises allowing a test cell and a substance to be tested to coexist, and detecting a change in a ligand-dependent interaction between the PPAR and a coactivator in the test cells due to the substance to be tested by measuring the expression of a reporter gene as an index.

DESCRIPTION OF THE PREFERRED EMBODIMENTS

Figure 1A:
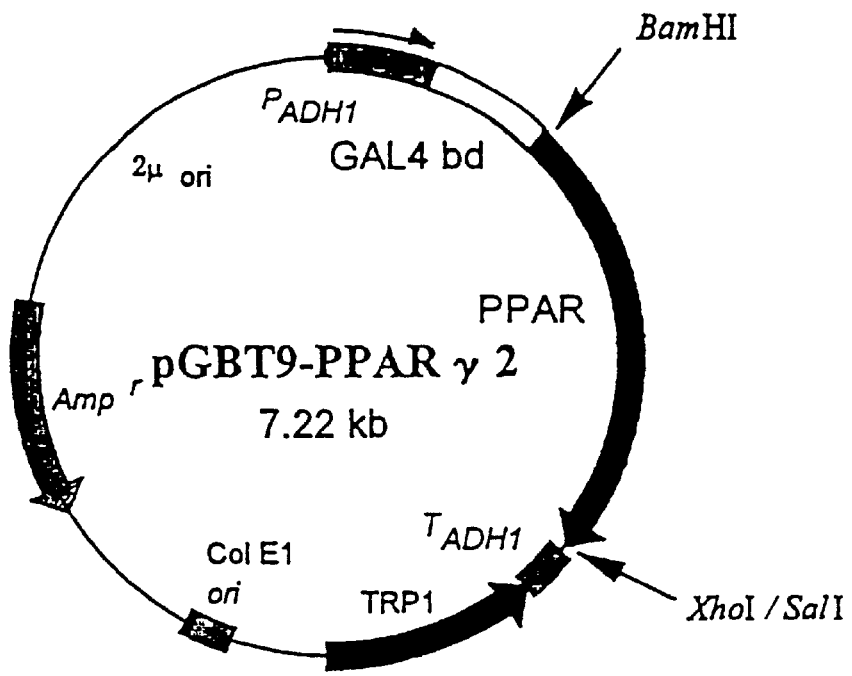
FIGS. 1A and 1B are schematic diagrams illustrating the constitutions of used plasmids pGBT9-PPARγ2 (FIG. 1A) and pGAD424-CBP (FIG. 1B)

In this invention, a ligand-dependent interaction between PPAR and a coactivator in the test cells is detected. PPAR changes its conformation into an activated type by binding to a ligand and the interaction with a coactivator takes place. That is, the ligand-dependent interaction is the binding of PPAR with the coactivator promoted in the presence of a ligand of PPAR.

As PPAR, subtypes such as PPARα, PPARδ (or NUC-1, PPARβ, FAAR) and PPARγ are known. In this invention, any one of these subtypes can be used. Among these, PPARγ is a target molecule of thiazolidinedione derivatives having an antidiabetic effect. A method for identifying or screening a specifically acting agent therefor is useful in research and development of a remedy for diabetes mellitus.

PPAR may be derived from any species so far as it is identified as the same molecular species and exhibits its function in the organism as a nuclear receptor. For example, it includes those derived from mammalians such as human, mouse, rat, hamster, etc., and in addition those derived from clawed toad (Xenopus laevis). From the point of view of utilizing research and development of a remedy for humans, it is preferred to use human-derived one out of these.

The gene sequences and amino acid sequences of PPARα (Dreyer et al., Cell, vol. 68, pp. 879–887, 1992, Green et al., Nature, vol. 347, pp. 645–650, 1990, Goettlicher et al., Proc. Natl. Acad. Sci. USA, vol. 89, pp. 4653–4657, 1992), PPARδ (or NUC-1, PPARβ, FFAR) (Dreyer et al., Cell, vol. 68, pp. 879–887, 1992, Kliewer et al., Proc. Natl. Acad. Sci. USA, vol. 91, pp. 7355–7359, 1994, Amri et al., Journal of Biological Chemistry, vol. 270, pp. 2367–2371, 1995, Xing et al., Biochem. Biophys. Res. Commun., vol. 217, pp. 1015–1025, 1995) and PPARγ (Dreyer et al., Cell, vol. 68, p. 879–887, 1992, Zhu et al., Journal of Biological Chemistry, vol. .268, pp. 26817–26820, 1993, Kliewer et al., Proc. Natl. Acad. Sci., USA, vol. 91, pp. 7355–7359, 1994, Mukherjee et al., Journal of Biological Chemistry, vol. 272, pp. 8071–8076, 1997, Elbrecht et al., Biochem. Biophys. Res. Commun., vol. 224, pp. 431–437, 1996, Chem et al., Biochem. Biophys. Res. Commun., vol. 196, pp. 671–677, 1993, Tontonoz et al., Genes & Development, vol. 8, pp. 1224–1234, 1994, Aperlo et al., Gene, vol. 162, pp. 297–302, 1995) have already been reported. PPARγ includes two kinds of isoforms, PPARγ1 and PPARγ2. PPARγ1 as compared with PPARγ2 is deleted of 30 amino acids on the N-terminal side but the other amino acid sequence is quite the same. Each is expressed in an adipose tissue.

Among the reports, presuming from the homology with other nuclear receptor, etc., the ligand binding domain (LBD) of PPAR is considered to correspond to the domain including about No. 167 to 468 amino acids from the N-terminal side in the case of PPARα, to the domain including about No. 138 to 440 amino acids from the N-terminal side in the case of PPARδ, and the domain including about No. 174 to 475 amino acids from the N-terminal side in the case of PPARγ (corresponding to about residues 174 to 475 of SEQ ID NO:6).

To detect the interaction between PPAR and coactivator, a polypeptide including at least the ligand binding domain may be used. Cut and use of a polypeptide including the ligand binding domain of PPAR can exclude nonspecific interaction and hence are preferred.

The coactivator used in this invention may be any one so far as it interacts with PPAR ligand-dependently, that is, the interaction with PPAR in the presence of a ligand of PPAR is promoted. The coactivator which is considered to interact with nuclear receptor includes, for example, CBP, SRC-1, RIP140 (Cavailles et al., EMBO Journal, vol. 14, pp. 3741–3751, 1995), TIFI (Douarin et al., EMBO Journal, vol. 14, pp. 2020–2033, 1995, Vom Baur et al., EMBO Journal, vol. 15, pp. 110–124, 1996), TIF2 (Voegel et al., EMBO Journal, vol. 15, pp. 3667–3675, 1996), SUGI (Vom Baur et al., EMBO Journal, vol. 15, pp. 110–124; 1996), P300 (Chakravarti et al., Nature, vol. 383, pp. 99–103, 1996), etc. These are expected to interact also with PPAR ligand-dependently. The coactivator which is considered to interact specifically with PPARγ includes, for example, PGC-1 (PPAR gamma coactivator-1) (Puigserver et al., Cell, vol. 92, pp. 829–839, 1998), PGC-2 (PPAR gamma coactivator-2) (Cactillo et al., EMBO Journal, vol. 18, pp. 3676–3687, 1999), etc. These are expected to interact with PPARγ ligand-dependently.

Among these, CBP and SRC-1, as shown in Examples in the present specification later on and in the report by Krey et al., have been confirmed to interact with PPAR and can be used advantageously in this invention.

CBP (CREB-binding protein) is a protein that has been originally identified as a coactivator of transcription factor CREB (cAMP-regulated enhancer binding protein) that binds to CRE (cAMP-regulated enhancer) and both gene (SEQ ID Nb:7 for mouse and SEQ ID NO:9 for human) and amino acid (SEQ ID NO:8 for mouse and SEQ ID NO:10 for human) sequences thereof have been known (Chrivia et al. Nature, vol., 365, pp. 855–859, 1993; Kwok et al., Nature, vol. 370, pp. 223–226). Recently, it has been revealed that CBP binds not only to CREB but also to a nuclear receptor in the presence of a ligand to serve as a coactivator and that the N-terminal moiety of CBP participates in the interaction with the nuclear receptor (Kamei et al., Cell, vol. 85, pp.

403–414, 1995). That the N-terminal moiety of CBP interacts also with PPARγ ligand-dependently was found uniquely by the present inventors.

SRC-1 is known to interact with nuclear receptors such as glucocorticoid receptor, estrogen receptor, thyroid hormone receptor and retinoid X receptor (RXR) ligand-dependently and serves as a coactivator. Its gene and amino acid sequence are also known (Onate et al., Science, vol. 270, pp. 1354–1357, 1995). In the Krey et al. report (Molecular Endocrinology, vol. 11, pp. 779–791, 1997), the experiment using the ligand binding domain of clawed toad (Xenopus laevis-derived PPAR and RI-labeled SRC-1 indicated that PPAR also interacts with SRC-1 ligand-dependently.

Upon detecting the ligand-dependent interaction with PPAR, the whole coactivator may be used, besides, a polypeptide that contains at least PPAR binding domain (the domain that participates in binding to PPAR) may be used. Coactivators generally have large molecular weights and use of the whole sometimes result in difficulty of expression of protein and it is preferred that appropriate domain be selected and used from this point of view.

The PPAR binding domain (domain participating in binding to PPAR) of a coactivator can be guessed from information on the position of its binding domain with a nuclear receptor if such an information has been reported. Also, using a system for detecting protein-protein interaction (for example, two-hybrid system of yeast), presence or absence of the interaction of a certain domain with PPAR may be examined and selection of a proper domain may be made. In the case where the coactivator is CBP, then PPAR binding domain exists near the N-terminal moiety (domain including about No. 1 to 450 amino acids).

In the present invention, the ligand-dependent interaction between PPAR and coactivator is detected in test cells using the expression of a reporter gene as an index and measurement was made of a change in the interaction due to the substance to be tested.

Noticing the interaction between PPAR and coactivator, the transcription activation effect of PPAR per se is not detected, so that various factors inherent to mammals participating in the expression of transcription activation ability of PPAR do not have to be present. Therefore, there is no need to use mammalian cells as test cells. Cells may be any one so far as they are eucaryotic cells. For example, there may be mentioned yeast cells, insect cells, mammalian cells, etc. Among these, yeast cells are advantageous in that their cultivation is easy and can be performed quickly and that application of genetic recombination technique such as introduction of extrinsic genes is easy. As yeast cells, there can be used cell lines of microbes belonging to the genera Saccharomyces, Schizosaccharomiyces, etc., such as *Saccharomyces cerevisiae, Schizosaccharomiyces pombe*, etc.

As the test cells, usually those that contain extrinsic PPAR and coactivators may be used. Use of cells containing no intrinsic PPAR or coactivators interacting therewith is preferred since the influence due to intrinsic elements can be excluded.

The change in the interaction between PPAR and coactivator due to the substance to be tested can be efficiently measured by a method utilizing a two-hybrid system.

The two-hybrid system is a method for detecting protein-protein interaction using the expression of a reporter gene as a marker (U.S. Pat. No. 5,283,173 and Proc. Natl. Acad. Sci., USA, vol. 88, pp. 9578–9582, 1991). Many transcription factors can be divided into two domains having different functions, that is, a DNA binding domain and a transcriptional activation domain. In the two-hybrid system, for example, to examine the interaction between the two proteins X and Y, two kinds of fused protein, that is, a fused protein composed of the DNA binding domain of a transcription factor and X, and a fused protein composed of the transcriptional activation domain of a transcription factor and Y are simultaneously expressed in yeast cells. When the proteins X and Y interact with each other, the two kinds of fused proteins form by combination a transcription complex exhibiting a single function as a whole. This transcription complex combines with a response element (the site of DNA to which a transcription factor is bound specifically) in the nuclei of cells and activates transcription of a reporter gene positioned downstream. Thus, the interaction between the two proteins can be detected by the expression of the reporter gene (for example, the enzyme activity of gene products).

The two-hybrid system can usually be used in the identification of unknown proteins that interact with a specific protein and generally used in qualitative evaluation of protein-protein interaction. The present inventors utilized this system, and thus, completed a method which can quantitatively measure the ligand-dependent interaction between PPAR and a coactivator, and can be applied to the identification or screening of antagonist/agonist for receptors, in which quantitative evaluation is indispensable.

As one embodiment of the present invention, there may be mentioned a method for identifying an agonist for or an antagonist to PPAR, comprising: using test cells containing (i) a first fused gene coding for a first fused protein comprising at least ligand binding domain of PPAR and a first domain of a transcription factor, wherein the first domain of said transcription factor being a DNA binding domain or a transcriptional activation domain;

(ii) a second fused gene coding for a second fused protein comprising at least PPAR binding domain of a coactivator which interacts with the PPAR and a second domain of the transcription factor, wherein the second domain of said transcription factor is a transcriptional activation domain when the first domain of the transcription factor is a DNA binding domain or is a DNA binding domain when the first domain of the transcription factor is a transcriptional activation domain, and (iii) a response element to which the DNA binding domain of said transcription factor can bind and a reporter gene linked thereto, making the test cells coexist with a substance to be tested, and detecting, by measuring the expression of a reporter gene as an index, a change in the ligand-dependent interaction between the peroxisome proliferator-activated receptor (PPAR) and a coactivator in the test cells occurring due to the substance to be tested.

In this embodiment, the transcription factor used for detecting the interaction between the PPAR and coactivator is not limited particularly so long as it is a transcription factor (other than PPAR) of eucaryotic organism that can exhibit the function of transcriptional activation in cells. However, it is preferred to use a transcription factor derived from yeast from the viewpoint that it does not need the coactivator, etc. derived from mammalian cells to function and it independently exhibits transcriptional activation ability efficiently in yeast cells.

Such a transcription factor includes yeast GAL4 protein (Keegan et al., Science, vol. 231, pp. 699–704, 1986, Ma et al., Cell, vol. 48, pp. 847–853, 1987), GCN4 protein (Hope et al., Cell, vol. 46, pp. 885–894, 1986), ADR1 protein (Thukral et al., Molecular and Cellular Biology, vol. 9, pp. 2360–2369, 1989), etc.

The DNA binding domain of the transcription factor may be those having a DNA binding ability to the response element but alone having no transcriptional activation ability. Also, the transcriptional activation domain of the transcription factor may be those having a transcriptional activation ability but alone having no DNA binding ability to the response element.

The DNA binding domain and transcriptional activation domain of a transcription factor, in the case of, for example, GAL4, are known to be present on the N-terminal side (a domain including about No. 1 to 147 amino acids) and C-terminal side (the domain including about No. 768 to 881 amino acids), respectively. In the case of GCN4, they are known to be present on the C-terminal side (the domain including about No. 228 to 265 amino acids) and N-terminal side (the domain including about No. 107 to 125 amino acids), respectively. In the case of ADR1, they are known to be present on the N-terminal side (the domain including about No. 76 to 172 amino acids) and the C-terminal side (the domain including about No. 250 to 1323 amino acids), respectively.

As the response element, a response element corresponding to a transcription factor may be used and DNA sequences to which the DNA binding domain of the transcription factor can bind are used. The response element corresponding to a transcription factor generally exists in a domain upstream of the gene whose transcriptional activity is controlled by the transcription factor, so that such a domain may be cut out for use. If its sequence is known, corresponding oligonucleotide may be synthesized by chemical synthesis and used.

For example, in case of GAL4 is used as a transcription factor, GAL4-specific DNA sequence called UASg (upstream activation site of galactose genes) may be used as the response element. UASg is contained in the domain upstream of galactose metabolism genes such as the GAL1 gene, etc., so that these domains may be used. Alternatively, a nucleotide sequence corresponding to UASg may be chemically synthesized and used.

The reporter gene positioned downstream of the response element is not limited particularly so far as it is a commonly used one and it is preferred to use the gene of an enzyme which is stable and allows easy quantitative measurement of its activity, etc. Such a reporter gene includes, for example, β-galactosidase gene (lacZ) derived from *E. coli*, chloramphenicol acetyltransferase gene (CAT) derived from bacterial transposone, luciferase gene (Luc) derived from a firefly, etc. Among these, *E. coli*-derived β-galactosidase gene (lacZ) is preferable since it can be readily measured with visible light using a coloring substrate. The reporter gene may be a gene having an original promoter of the gene, or besides, a gene of which promoter part is replaced with one derived from of another gene may be used. The reporter gene may be enough if it is operatively linked downstream of the response element.

The first fused protein contains the ligand binding domain of PPAR and the first domain of the transcription factor (DNA binding domain or transcriptional activation domain) and the second fused protein contains the PPAR binding domain of a coactivator and the second domain of transcription factor (transcriptional activation domain or DNA binding domain). The two kinds of domains constituting the fused protein may be each arranged in the upstream domain. The fused protein may have additional construction or deletion or substitution of sequence within the range that necessary functions are not damaged.

The first and second domains of the transcription factor must be integrated before they can bind to the response element and play the function of activating gene transcription. For this purpose, when the first domain is a DNA binding domain, the second domain must be a transcriptional activation domain. When the first domain is a transcriptional activation domain, the second domain must be a DNA binding domain. The first and second domains do not necessarily be derived from the same transcription factor but may be derived from different transcription factors.

The fused genes coding for the first and second fused proteins may be designed and constructed by using a usual genetic recombination technique. As for the DNA coding for the ligand binding domain of PPAR, PPAR binding domain of a coactivator, DNA binding domain of a transcription factor and transcriptional activation domain of a transcription factor constituting the first and second fused proteins, cDNA may be isolated from cDNA library by, for example, screening, etc., using PCR (Polymerase Chain Reaction) or a synthetic probe which uses a primer or probe designed and synthesized based on the information on the known amino acid sequence or nucleotide sequence. DNAs coding for the respective domains are linked and the resulting material is linked downstream of a suitable promoter to construct a fused gene. To each domain or DNA coding this, it may be introduced addition, deletion, substitution of sequence within the range where necessary functions are not damaged.

The resulting first and second fused genes may be incorporated into a suitable vector plasmid and introduced into host cells in the form of a plasmid. The first and second fused genes may be constructed so as to be contained on the same plasmid or on separate plasmids.

The response element and the reporter gene linked thereto may also be designed, constructed using usual genetic recombination technique and the construction is incorporated into the vector plasmid, and the resulting recombinant plasmid may be introduced into host cells. Alternatively, cells in which such a construction is incorporated in chromosomal DNA may be acquired and used.

Test cells including all the constitution may be acquired, for example, by introducing one or more plasmids containing the first and second fused genes into host cells in which a response element along with a reporter gene linked thereto are introduced into the chromosomal DNA of the host cells.

The thus obtained test cells are cultivated, for example, in the presence of a substance to be tested, and an interaction between PPAR and a coactivator is detected and measured by the expression of the reporter gene. When the substance to be tested binds to PPAR and an interaction with the coactivator occurs depending on the binding, an increase in the reporter activity is observed. Such a substance to be tested can be identified as an agonist for PPAR. For example, when the substance to be tested binds to PPAR but does not promote the interaction with the coactivator, addition of it together with true ligand or the drug identified as an agonist, a decrease in the reporter activity expressed by the true ligand or agonist is observed. Such a substance to be tested is identified as an antagonist to PPAR.

Of the invention, as another embodiment of the method in which the ligand-dependent interaction with CBP is detected and the effect of a substance to be tested is measured with respect to said interaction, there is, for example, a method in which the ligand-dependent interaction between PPAR and CBP is measured directly. In this method, for example, CBP or its PPAR binding domain labeled with RI, etc. is used and the binding with a fused protein composed of a suitable tag protein, such as glutathione-S-trans-ferase (GST), protein A, β-galactosidase, and maltose-binding protein (MBP), and the ligand binding domain of PPAR is directly detected in the presence of the substance to be tested.

According to the method of the invention, for example, screening for an acting agent against PPARγ can be performed. As the ligand for PPARγ, various types of thiazolidinedione derivatives have been identified and prostaglandin, 15d-PGJ$_2$ (15-deoxy-Δ12,14-prostaglandin J$_2$), one of arachidonic acid metabolites, is considered to be a true ligand (Cell, vol. 83, pp. 803–812 and pp. 813–819, 1995). Therefore, upon the identification or screening of an agonist for PPARγ, 15d-PGJ$_2$ can be used as a positive control. By examining presence or absence of inhibition against ligand-dependent interaction expressed by 15d-PGJ$_2$, the identification or screening of antagonist to PPARγ can be practiced.

The agonist for PPARγ is expected as a remedy for treating diabetes having excellent hypoglycemic effect. Since PPARγ is an inducing factor for differentiation of adipocytes, the antagonist to PPARγ is expected to have effect as an anti-obese agent.

Upon screening PPARγ acting agents, the effect on other subtypes, that is, PPARα or PPARδ (or NUC-1, PPARβ, FAAR) is inspected, whereby medicines having a high selectivity for PPARγ can be selected.

EXAMPLES

In the following, the invention will be explained in more detail by referring to Examples. However, the present invention is not limited thereto.

In the following examples, unless otherwise specified particularly, each operation was according to the method described in "Molecular Cloning" (written by Sambrook, J., Fritsch, E. F. and Maniatis, T., published by Cold Spring Harbor laboratory Press in 1988) was followed, or when commercially available reagent or kit was used, they were used according to the commercially available specification.

Example 1

Construction of PPARγ acting agent screening system based on ligand-dependent interaction between PPARγ and CBP (1) Isolation of genes of PPARγ2 and CBP cDNA of PPARγ2 was acquired from cDNA library (available from Clontech Co.) By the PCR method. In the PCR, the following primers of SEQ ID NOs: 1 and 2 in the Sequence Listing shown below were used. These primers were designed based on the gene sequence of human PPARγ2 described in Accession No. D83233 (SEQ ID NO:5) of gene database, Genbank, and a restriction enzyme recognition site for inserting into yeast expression vector was added to the terminal of the primer. The resulting 1574 base pair fragment had a SmaI recognition site before the start codon and a XhoI recognition site after the stop codon, this coding for full-length human PPARγ2.

The cDNA at the N terminus of CBP was obtained by the PCR method from cDNA obtained by reverse transcription reaction from RNA prepared from mouse adipocytes. In the PCR, the primers shown in SEQ. ID. NOs: 3 and 4 in the Sequence Listing shown below were used. These primers were designed based on the gene sequence of mouse CBP described in the literature by Chrivia et al. (Nature, vol. 365, 855–859, 1993) to the termini of the primer being added a restriction enzyme recognition site for insertion into yeast expression vector. The resulting 1411 base pair fragment had a BamHI recognition site before the start codon and a BglII recognition site at the C terminus, and coding for the No. 1 to 464 amino acids of mouse CBP.

(2) Construction of expression vector for fused protein comprising ligand binding domain of PPARγ and DNA binding domain of GAL4

The 1574 base pair fragment containing PPARγ2 gene obtained in (1) above was cleaved at the XhoI recognition site designed at the terminus and the BamHI recognition site in the base sequence. The fragments obtained were inserted into the BamHI-SalI site of yeast expression vector pGBT9 (available from Clontech Co., vector for yeast two hybrid system) containing the gene of the DNA binding domain of transcription factor GAL4 (No. 1 to 147 amino acid residues of GAL4). As a result, plasmid pGBT9-PPARγ2 (FIG. 1A) for expressing a fused protein comprising the portion downstream of the No. 181 amino acid residue of human PPARβ2 (ligand binding domain) and the DNA binding domain of GAL4 was obtained. In FIG. 1A, GAL4 bd stands for a GAL4 DNA binding domain sequence, $^P$ADH1 stands for alcohol dehydrogenase gene promoter, $^T$ADH1 stands for an alcohol dehydrogenase gene terminator, Ampr stands for an ampicillin resistant gene, ColE1 ori stands for a collicin E1 replication start point, and 2 μ ori stands for a 2 μ replication start point.

(3) Construction of expression vector for fused protein comprising the N-terminal domain of CBP (PPAR binding domain) and the transcriptional activation domain of GAL4

Figure 1B:
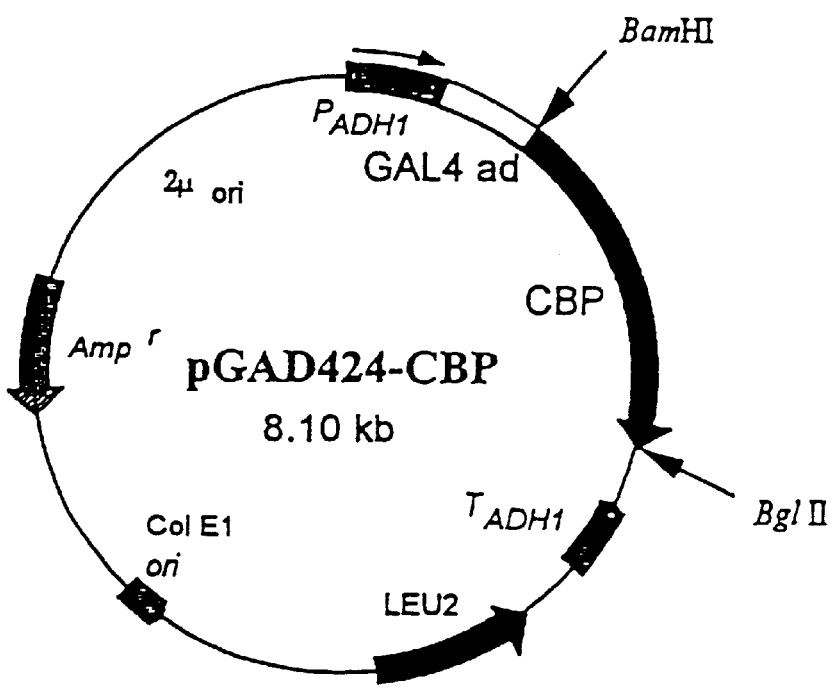

The 1411 base pair fragment containing CBP gene obtained in (1) above (N-terminal domain) was cleaved at the BamHI recognition site and BglII recognition site designed at the termini. The fragments obtained were inserted into the BamHI-BglII site of yeast expression vector pGAD424 (available from Clontech Co., vector for yeast two hybrid system) containing the gene of the transcriptional activation domain of GAL4 (No. 768 to 881 amino acid residues of GAL4). As a result, plasmid pGAD424-CBP (FIG. 1B) for expressing a fused protein comprising the portion of the No. 1 to 464 amino acid residues of mouse CBP (N-terminal domain) and the transcriptional activation domain of GAL4 was obtained. In FIG. 1B, GAL4 ad stands for GAL4 transcriptional activation domain sequence and others have the same meanings as in FIG. 1A.

(4) Transformation of yeast

Using yeast cell strain SFY526 (available from Clontech Co.), the fused protein expression plasmids pGBT9-PPARγ2 and pGAD424-CBP obtained in (2) and (3) above were introduced therein. The cell strain SFY526 (genotype was MATa, ura3-52, his3-200, ade2-101, lys2-801, trp1-901, leu2-3, 112, canr, gal4-542, gal80-538, URA3::GAL1-lacZ) had incorporated in the chromosome a fused gene of GAL1 and lacZ and is a cell strain having deletion mutation relative to GAL4 gene (Bartel et al., Bio Techniques, vol. 14, pp. 920–924, 1993). The transformation was performed by the lithium acetate method and incubated in a synthetic medium depleted of tryptophan and leucine which are selection markers for the respective plasmids to perform screening to obtain a transformant in which only one of the plasmids was introduced and a transformant in which the both plasmids were introduced.

(5) Detection of ligand-dependent interaction between PPARγ and CBP

The yeast transformant containing both of the plasmids pGBT9-PPARγ and pGAD424-CBP or the yeast transformant containing only one of the plasmids was cultivated in YPD medium (liquid medium). Upon cultivation, 15-deoxy-Δ12,14-prostaglandin J$_2$, which is a ligand of PPARγ2 in a living body, diluted with YPD medium was added (or not added). 15-deoxy-Δ12,14-prostaglandin J$_2$ (hereinafter abbreviated to as "15d-PGJ$_2$") used was commercially available (available from CAYMAN CHEMICALS, CO., U.S.A.). The cultivation was performed for 4 to 5 hours. After the cultivation, the yeast cells were recovered by centrifugation and β-galactosidase activity was measured.

Figure 2A:
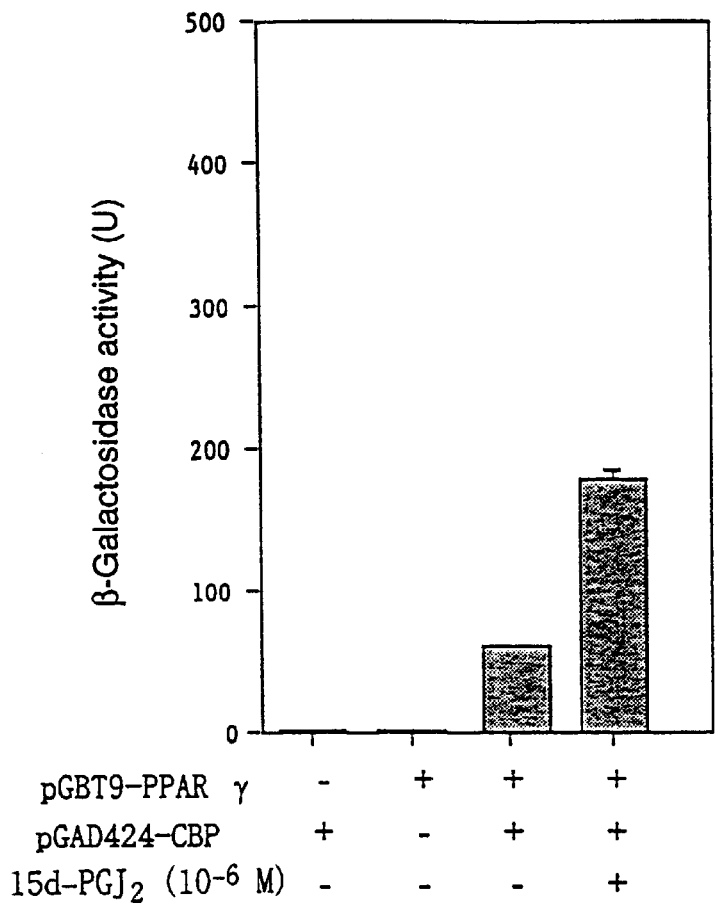
FIGS. 2A and 2B are diagrams illustrating ligand-dependent interaction between PPARγ and CBP (FIG. 2A), and dose-dependent effects of 15d-PGJ$_2$ (FIG. 2B)
Figure 2B:
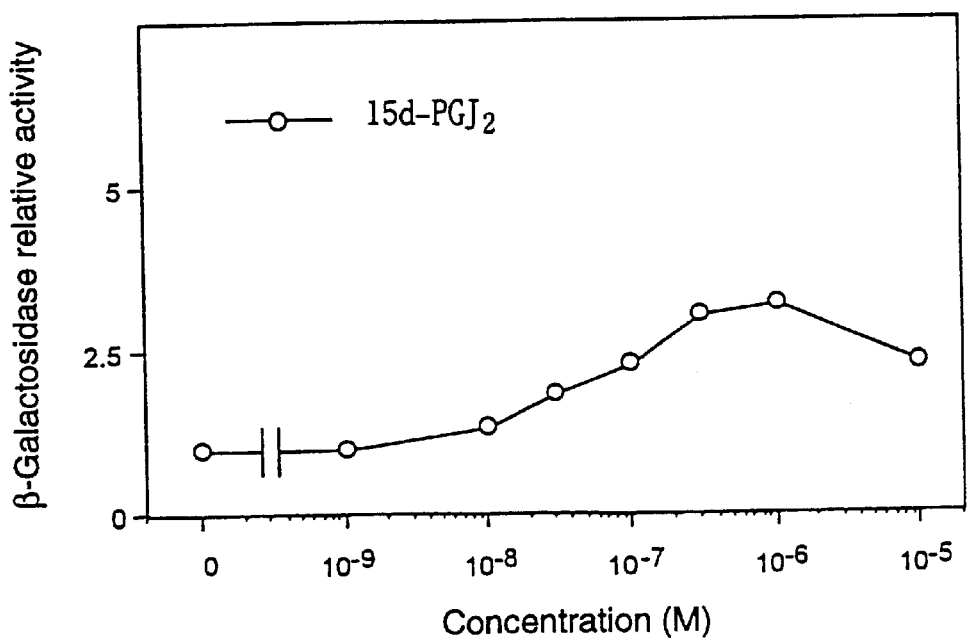

As a result, by the addition of 15d-PGJ$_2$, an increase in β-galactosidase activity (lacZ gene expression) in yeast containing both of the plasmids pGBT-PPARγ and pGAD424-CBP was observed (FIG. 2A). Such an increase in β-galactosidase activity due to 15d-PGJ$_2$ was observed dependent on the concentration of 15d-PGJ$_2$ (FIG. 2B). These were considered to be attributable to the ligand-dependent interaction between PPARγ and CBP due to the presence of the ligand, 15d-PGJ$_2$. From this result, it revealed that the N-terminal domain of CBP interacts with PPAR. Further, it was considered that in this system, the ligand-dependent interaction between PPARγ and CBP could be detected and measured.

Next, using as a substance to be tested thiazolidinedione derivative T-174 (chemical name: 5-[[2-(2-naphthalenylmethyl)-5-benzoxazolyl]methyl]-2,4-thiazolidinedione) represented by the following formula:

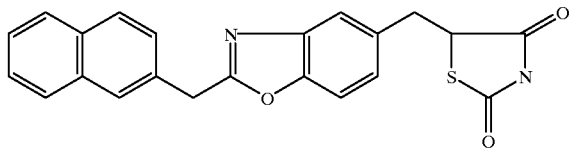

its effect on PPARγ was examined.

In the same manner as mentioned above, the yeast transformant containing both of the plasmids pGBT9-PPARγ and pGAD424-CBP or a yeast transformant containing only one of the plasmids was cultivated. However, upon cultivation, T-174 was added as a substance to be tested instead of 15d-PGJ$_2$ in the medium. T-174 used was synthesized by a method similar to that described in Japanese Provisional Patent Publication No. 56675/1989 (Example 49).

Figure 3A:
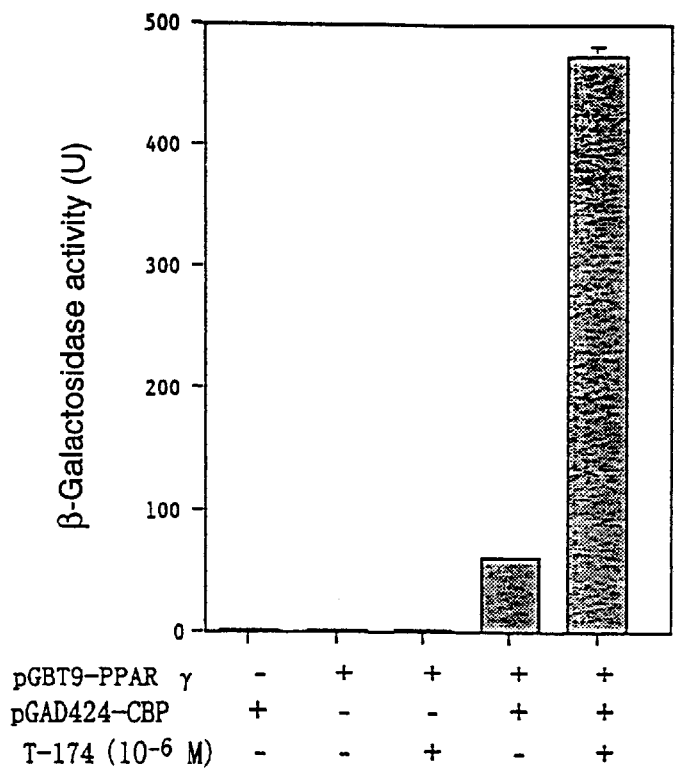
FIGS. 3A and 3B are diagrams illustrating action of T-174 to the interaction between PPARγ and CBP (FIG. 3A) and dose-dependent effects of T-174 (FIG. 3B).
Figure 3B:
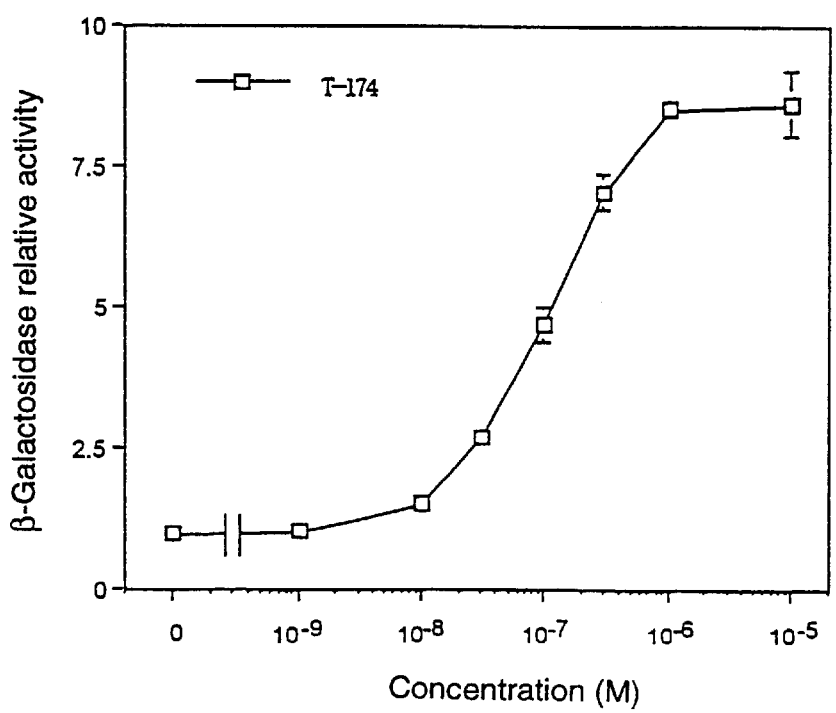

As a result an increase in β-galactosidase activity was observed only in the yeast containing both of the plasmids pGBT-PPARγ and pGAD424-CBP (FIG. 3A). Its effect was dependent on the concentration of T-174 (FIG. 3B). Thus, the ligand-dependent interaction between PPARγ and CBP was detected due to the presence of T-174, so that T-174 was identified as an agonist acting as a ligand to PPARγ.

T-174 is known to have a hypoglycemic effect in a disease model of mouse (KK-Ay mouse) (Japanese Provisional Patent Publications No. 56675/1989 and No. 167225/1990). Although its acting point was unclear, the above results indicate that the acting target molecule of T-174 is PPARγ.

Example 2

Construction of PPARγ acting agent screening system based on the ligand-dependent interaction between PPARγ and SRC-1 cDNA of the full domain of SRC-1 is obtained by the PCR method from the cDNA library prepared from human adipose tissue. The primers are designed based on the gene sequence of human SRC-1 described in the literature of Onate et al. (Science, vol. 270, pp. 1354–1357, 1995) and to the terminus of the primer is added a restriction enzyme recognition site for insertion of yeast expression vector.

This is used instead of the cDNA of CBP and, in the same manner as in Example 1 (2) and (3), the cDNA of PPARγ2 is inserted into the yeast expression vector pGBT9 and the cDNA of SRC-1 is inserted into the yeast expression vector pGAD424, respectively, whereby an expression vector for a fused protein comprising the ligand binding domain of PPARγ and the DNA binding domain of GAL4, and an expression vector a fused protein comprising the full domain of SRC-1 and the transcriptional activation domain of GAL4 are constructed.

The resultant two kinds of fused protein expression plasmid are introduced into yeast cell strain SFY526 of which a fused gene of GALL and lacZ is incorporated in its chromosome and having a deletion mutation regarding GAL4 gene in the same manner as in Example (4) above.

Using the obtained transformed strain, the ligand-dependent interaction between PPARγ and SRC-1 is detected in the same manner as in Example (5) above.

INDUSTRIAL APPLICABILITY

The conventional identification method for PPAR acting agent detecting the transcriptional activation ability of PPAR in the cells accepts participation of a coactivator and RXR which are intrinsic to the cells. The method of this invention is free from this participation, so that only the effect of the substance to be tested to PPAR can be detected with accuracy. Also, the method of the invention does not have to use mammalian cells and can use yeast cells as well, so that cultivation operations can be performed with ease and quickly. Further, there is no need for using radioisotope-labeled compound to be tested or protein and hence the method is safe and simple.

According to the method of the invention, since it is possible to treat a number of substances to be tested simultaneously with sufficient sensitivity and quantitativeness, the identification and screening of agonist for and antagonist to PPAR can be performed efficiently.

What we claimed is:

1. A method for identifying or screening an agonist for, or an antagonist to, a human peroxisome proliferator-activated receptor gamma (PPARγ), which comprises contacting a test cell with a substance to be tested, and detecting a change in a ligand-dependent interaction between the human PPARγ and a coactivator due to the substance to be tested, by measuring the expression of a reporter gene as an index, wherein the test cell contains:
   (i) a first extrinsic fused gene coding for a first fused protein comprising a ligand binding domain of human PPARγ and a first domain of a transcription factor, wherein the first domain of said transcription factor being a DNA binding domain or a transcriptional activation domain;
   (ii) a second extrinsic fused gene coding for a second fused protein comprising a human PPARγ binding domain of a coactivator which interacts with the human PPARγ and a second domain of the transcription factor, wherein the second domain of said transcription factor is a transcriptional activation domain when the first domain of the transcription factor is a DNA binding domain or is a DNA binding domain when the first domain of the transcription factor is a transcriptional activation domain; and
   (iii) a response element to which the DNA binding domain of said transcription factor can bind and a reporter gene linked thereto, and
   wherein the coactivator is CREB-binding protein (CBP).

2. The method according to claim 1, wherein the test cell is a yeast cell.

3. The method according to claim 1, wherein the ligand binding domain of human PPARγ comprises residues 174 to 475 of SEQ ID NO:6.

4. The method according to claim 1, wherein human PPARγ comprises the amino acid sequence of SEQ ID NO:6.

5. The method according to claim 1, wherein the CBP has the amino acid sequence of SEQ ID NO:8.

6. The method according to claim 1, wherein the CBP has the amino acid sequence of SEQ ID NO:10.

* * * * *